United States Patent [19]
Friedman et al.

[11] Patent Number: 5,447,852
[45] Date of Patent: Sep. 5, 1995

[54] DNA ENCODING CYCLOPHILIN C, AND RECOMBINANT METHODS EMPLOYING IT

[75] Inventors: Jeffrey S. Friedman, Portola Valley; Irving L. Weissman, Palo Alto, both of Calif.

[73] Assignee: The Board of Trustees of the Leland Stanford Junior University, Palo Alto, Calif.

[21] Appl. No.: 142,897

[22] Filed: Oct. 26, 1993

Related U.S. Application Data

[63] Continuation of Ser. No. 5,917, Jan. 15, 1993, abandoned, which is a continuation of Ser. No. 740,375, Aug. 5, 1991, abandoned.

[51] Int. Cl.$^6$ .................... C12N 15/12; C12N 15/61; C12N 15/62; C12N 5/10
[52] U.S. Cl. .................... 435/69.7; 435/69.1; 435/320.1; 435/240.2; 435/252.3; 536/23.2; 536/23.4
[58] Field of Search .................... 536/23.4, 24.32, 23.2; 435/69.1, 69.7, 320.1, 240.2, 252.3; 530/350

[56] References Cited

FOREIGN PATENT DOCUMENTS 0326067 2/0889 European Pat. Off. .

OTHER PUBLICATIONS

Hultsch, T., et al. (1991), "Immunophilin ligands demonstrate common features of signal transduction leading to exocytosis or transcription", *Proc. Natl. Acad. Sci. USA* 88: 6229–33.

DiLella, A. G. et al. (1991), "Exon organization of the human FKBP-12 gene: correlation with structural and functional protein domains", *Biochem.* 30: 8512–17.

Bergsma et al. A Chinese Hamster ovary cyclophilin. 1990. Nucl. Acids Res. 18:200.

Bierer et al., Probing Immunosuppressant Action with a Nonnatural Immunophilin Ligand, (1990) *Science* 250:556–559.

Danielson et al., p1B15: A cDNA Clone of the Rat mRNA Encoding Cyclophilin, (1988) *DNA* 7:261–267.

Dumont et al., The Immunosuppressive Marcolides FK-506 And Rapamycin Act As Reciprocal Antagonists In Murine T Cells, (1990) *The Journal of Immunology* 144:1418–1424.

Durette et al., A Study of the Correlation Between Cyclophilin Binding and In Vitro Immunosuppresive Activity of Cyclosporine A and Analogues, (1988) *Transplantation Proceedings* 2:51–57.

Emmel et al., Cyclosporin A Specifically Inhibits Function of Nuclear Proteins Involved in T Cell Activation, (1989) *Science* 246:1617–1620.

Fischer et al., Cyclophilin and Peptidyl-prolyl cis-trans Isomerase are Probaby Identical Proteins, (1989) *Nature* 337:476–478.

Harding et al., A Receptor for the Immuno-suppressant FK506 is a cis-trans Peptidyl-prolyl Isomerase, (1989) *Nature* 341:758–760.

(List continued on next page.)

*Primary Examiner*—Garnette D. Draper
*Assistant Examiner*—David L. Fitzgerald
*Attorney, Agent, or Firm*—Townsend and Townsend Khourie and Crew

[57] ABSTRACT

The cloning and characterization of a new binding protein class, cyclophilin C (cyp C) and homologous proteins, is provided which is capable of binding to, e.g., the immunosuppressive drug cyclosporin A (CsA). The pattern of cyp C mRNA expression differs from that of cyp A mRNA expression, with cyp C being expressed in a more restricted subset of tissues, including those tissues reported to be most affected by CsA therapy. A fusion protein containing, e.g., amino acids 16–212 of cyp C has peptidyl-prolyl-isomerase activity (PPIase), and CsA inhibits this activity. Most significantly, these cyp C fusion proteins can be used as ligands for the identification of intracellular proteins which together form high affinity associations. For example, the cyp C fusion protein binds specifically to a protein of 77 Kd in the absence of CsA, while in the presence of CsA it no longer binds to this p77, but instead binds specifically to a protein 55 Kd, identified as calcineurin.

17 Claims, 11 Drawing Sheets

OTHER PUBLICATIONS

Hasel et al., *Nucleotide Sequence of a cDNA Coding for Mouse Cyclophilin*, (1990) Nucl. Acids Res. 18:4019.

Haendler et al., Yeast Cyclophilin: Isolation and Characterization of the Protein, cDNA and Gene, (1989) *Gene* 83:39–46.

Hultsch et al., Cyclosporin A Inhibits Degradulation of Rat Basophilic Leukemia Cells and Human Basophils, (1990) *J of Immunology* 144:2659–2664.

Koletsky et al., Cyclophilin: Distribution and Variant Properties in Normal and Neoplastic Tissues, (1986) *J of Immunology* 137:1054–1059.

Koser et al., A Second Cyclophilin-Related Gene in Saccharomyces Cerevisiase, (1990) *Nucleic Acids Res* 18:1643.

Schneuwly et al., Drosophilia NinaA Gene Enclodes an Eye-Specific Cyclophilin (Cyclosporine A Binding Protein), (1989) *Proc. Natl. Acad. Sci.* 86:5390–5394.

Stuart L. Schreiber, Chemistry and Biology of the Immunophilins and Their Immunosuppressive Ligands, (Jan. 18, 1991) *Science* 251:283–287.

Shieh et al., The ninaA Gene Required for Visual Transduction in Drosophilia Encodes a Homologue of Cyclosporin A-Binding Protein, (1989) *Nature* 338:67–70.

Siekierka et al., A Cytosolic Binding Protein for the Immunosuppressant FK506 has Peptidyl-prolyl Isomerase Activity but is Distinct from Cyclophilin, (1989) *Nature* 341:755–757.

Sigal et al., Is Cyclophilin Involved in the Immunosuppressive and Nephrotoxic Mechanism of Action of Cyclosporin AP, (Mar. 1991) *J. Exp. Med.* 173:619–628.

Stamnes et al., The Cyclophilin Homolog ninaA Is a Tissue-Specific Integral Membrane Protein Required for the Proper Synthesis of a Subset of Drosophila Rhodopsins, (Apr. 19, 1991) *Cell* 65:219–227.

Takahasi et al., Peptidyl-Prolyl cis-trans Isomerase is the Cyclosporin A-Binding Protein Cyclophilin, (1989) *Nature* 337:473–475.

Tocci et al., The Immunosuppressant FK506 Selectively Inhibits Expression of Early T Cell Activation Genes, (1989) *J. of Immunology* 143:718–726.

Tropschug et al., Cyclosporin A-binding Protein (Cyclophilin) of Neutrospora Crassa, (1988) *J Biol. Chem.* 263:14433–14440.

Tropschug et al., Sensitivity to cyclosporin A is mediated by Cyclophilin in Neurospora Crassa and Saccharomyces Cerevisiae, (1989) *Nature* 342:953–955.

Whitlock et al., Bone Marrow Stromal Cell Lines with Lymphopoietic Activity Express High Levels of a Pre-B Neoplasia-Associated Molecule, (1987) *Cell* 48:1009–1021.

Liu et al., Calcineurin Is a Common Target of Cyclophilin-Cyclosporin A and FKBP-FK506 Complexes, (Aug. 23, 1991) *Cell* 66:807–815.

Friedman et al., Two Cytoplasmic Candidates for Immunophilin Action Are Revealed by Affinity for a New Cyclophilin: One in the Presence and One in the Absence of CsA, (Aug. 23, 1991) *Cell* 66:799–806.

Handschumacher et al., Cyclophilin: A Specific Cytosolic Binding Protein for Cyclosporin A, (1984) *Science* 226:544–547.

Haendler et al., Complementary DNA for Human T--Cell Cyclophilin, (1984) *EMBO J.* 6:947–950.

Price, Human Cyclophilin B: A Second Cyclophilin Gene Encodes a Peptidyl-Prolyl Isomerase With A Signal Sequence, Proc Natl Acad Sci USA (Mar. 1991) 88:1903–1907.

```
  1 CCCGAGCCTAAGGTTGCGCCCGTGCCATCGTTGCCACTTCCACCGGCACC ATG AGC CCG GGT CCC CGT CTG
                                                        1►Met Ser Pro Gly Pro Arg Leu

74 CTG CCC GCG GTG CTC TGC CTG GGG CTT GGA GCC CTG GTG TCT TCT TCG GGG AGG TCC TCA
  8►Leu Pro Ala Val Leu Cys Leu Gly Leu Gly Ala Leu Val Ser Ser Ser Gly Ser Ser

134 GGC GTC CGA AAA CGA GGT CCC GTG TCG GTG ACG AAG GTC TTC TTT GAT GTG AGG ATC GGA
 28►Gly Val Arg Lys Arg Gly Pro Val Ser Val Thr Lys Val Phe Phe Asp Val Arg Ile Gly

194 GAC AAA GAT GTG GGT AGA ATT GTG GGC CTC TTT GGA AAC GTT GTA CCC AAG ACG GTG
 48►Asp Lys Asp Val Gly Arg Ile Val Gly Leu Phe Gly Asn Val Val Pro Lys Thr Val

254 GGA AAC TTC GTG GCT CTG GCA ACA GGA GAG AAA GGC TAC AAG GAC TTC ACA AGC ATC TTC
 68►Glu Asn Phe Val Ala Leu Ala Thr Gly Glu Lys Gly Tyr Lys Asp Phe Thr Ser Ile Phe

314 CAC CGT GTC ATC AAG GAC TTC ATG ATT CAA GGA GGG GAT GAG GAA CTG AGA GAT GGC ACT
 88►His Arg Val Ile Lys Asp Phe Met Ile Gln Gly Gly Asp Glu Glu Leu Arg Asp Gly Thr

374 GGG ATG GGC ATC AGC ATC TAT GGT GAG ACA TTT CCG GAT GAG AAA TTC AAA CTG AAG CAC TAT
108►Gly Met Gly Ile Ser Ile Tyr Gly Glu Thr Phe Pro Asp Glu Lys Phe Lys Leu Lys His Tyr

434 GGC ATT GGC GTC TGG AGC ATG GCC AAT GCT GGA CCA GAC ACC AAC GGA TCC CAG TTC TTC
123►Gly Ile Gly Val Trp Ser Met Ala Asn Ala Gly Pro Asp Thr Asn Gly Ser Gln Phe Phe

494 ATC ACC TTG ACC AAG CCC ACC TGG TTG GAT GGC AAA CAC GTT GTA TTT GGA AAA GTC CTA
148►Ile Thr Leu Thr Lys Pro Thr Trp Leu Asp Gly Lys His Val Val Phe Gly Lys Val Leu

554 GAT GGG ATG ATG ACT GTG ACT GTA CAT CAT GAA CTT CAA GCA GAT ACA GAT GGC CAT CGC CCA
168►Asp Gly Met Gly Met Thr Val Thr Val His His Glu Leu Gln Ala Asp Thr Asp Gly His Arg Pro
```

FIG. 1-1.

```
614 CTC ACC GAC TGC ACC ATC GTC AAC AGT GGC AAG ATA GAT GTG AAA ACA CCC TTT GTG GTT
188►Leu Thr Asp Cys Thr Ile Val Asn Ser Gly Lys Ile Asp Val Lys Thr Pro Phe Val Val

674 GAG GTC CCT GAT TGG TGA CAGAAATGGCGAAGACAGGAAACACACTGGCCCATGTGCACATCTGTGATC
208►Glu Val Pro Asp Trp ...

748 CACCAGCAGTCTTTAGTTACTTAAAAGTTGTAGTTAAAAAAATTTCTCATTTAATTTCCAGTCTCGATTGCAATAACA
 828 AAATCAACACACAGTCAGATGTCTCAACAAACACCTGTCATCCCAGTATTTGGGAAGTGCAGGCAGGATCAGGGT
 908 TCAAGGCCAGCCTGGGCTAACAGTTTGAGGCCTTGTCTGTTACATAAGTAATAAGTAAAATCAATAAAATCAAA
 988 GTCCTGCTCAGAATTTTAAATTGAACGACATATCCTTCTTTCTAGTGGTGCTATTTTCAAATCAAAAAACTTTGCATT
1068 GGCTATTTGTTTTTACAAACATGTTGAGTTGTAGCATTTTCTGTTCCTTGTGATCTCCATTGGGTGACCCGAGGGTTTGTTTG
1148 AGGAAGGTGACTATAATGAAGGTTAGCATTTCTGTTCAGGCAAAGGGAAATTTGAGTAGTAGTATCA
1228 TATGCTGTATATCATGAGCATTCTGGGGCTTGTTCTTTATGTAAATACTTTTTAATC
```

FIG. 1-2.

| | | |
|---|---|---|
| YEAST CYP 2 | 1 | MKFSGLWCWLLLFLSVNVIASDVGELIDQDDEVITQKV`FFD`IEHGEEAV`GR``IVIGL` |
| HUMAN CYP B | 1 | MKVLLAAALLIAGSVFFLLLPGPSAADEKKKGPKVTVKV`YFD`LRIGDEDV`GR``VIFGL` |
| MURINE CYP C | 1 | MSPGPRLLLPAVLCLGLGALVSSSGSGVRKRGPSVTDKV`FFD`VRIGDKDV`GR``IVIGL` |
| MURINE CYP A | 1 | VNPTV`FFD`ITADDEPL`GR``VSFEL` |
| YEAST CYP 1 | 1 | MSQV`YFD`VEADGQPI`GR``VVFKL` |

| | | |
|---|---|---|
| YEAST CYP 2 | 57 | YGKVC`PKT`AKNFYKLSTT`TNSKKG`FIGST`FHR`VIPNFMV`QGGDFT`DGTGV`GGK`SIYG`DTFP` |
| HUMAN CYP B | 57 | FGKTV`PKT`VDNFVALAT`GEKGF`GYKNSK`FHR`VIKDFMI`QGGDFT`RGDGT`GGK`SIYG`ERFP` |
| MURINE CYP C | 59 | FGNVV`PKT`VENFVALAT`GEKGY`GYKGSI`FHR`VIKDFMI`QGGDFT`ARDGT`GGM`SIYG`ETFP` |
| MURINE CYP A | 24 | FADKV`PKT`AENFRALST`GEKGF`GYKGSS`FHR`IIPGFMC`QGGDFT`RHNGT`GGR`SIYG`EKFE` |
| YEAST CYP 1 | 23 | YNDIV`PKT`AENFRALCT`GEKGF`GYAGSP`FHR`VIPDFML`QGGDFT`AGNGT`GGK`SIYG`GKFP` |

FIG. 2-1.

| | | | | | | |
|---|---|---|---|---|---|---|
| YEAST CYP 2 | 118 | DENF TLKH DRK G RI SMAN R GKD TNGSQFFI TTTEEAS WLDGKHVVFG Q VDGM DV V NYI |
| HUMAN CYP B | 117 | DENF KLKH YGPG WV SMAN A GKD TNGSQFFI TT VKTA WLDGKHVFG K VLEG MEV V RKV |
| MURINE CYP C | 119 | DENF KLKH YGI GWV SMAN A GPD TNGSQFFI T LTKPT WLDGKHVVFG K VLDG MTV V HSI |
| MURINE CYP A | 84 | DENF ILKH TPG GI I SMAN A GPN TNGSQFFI CTAKTE WLDGKHVVFG K VKEG MNI V EAM |
| YEAST CYP 1 | 83 | DENF KKKH H DRP GLL SMAN A GPN TNGSQFFI TTVPCP WLDGKHVVFG E VDG YDI V KKV |

```
YEAST  CYP 2   177 QHVSRDANDKPLEAVKIAKCGEWTPELSS
HUMAN  CYP B   175 ESTKTDSRDKPLKDVIIADCGKIEVEKPFAIAKE
MURINE CYP C   177 ELQATDGHDRPLTDCTIVNSGKIDVKTPFVVEVPDW
MURINE CYP A   142 ERFGSRNGKTSKKITISDCGQL
YEAST  CYP 1   141 ESLGSPSGATKARIVVAKSGEL
```

FIG. 2-2.

DNA ENCODING CYCLOPHILIN C, AND RECOMBINANT METHODS EMPLOYING IT

This invention was made in the course of work supported by the U.S. Government, which has certain rights in this invention.

This is a continatuion of application Ser. No. 08/005,917, filed Jan. 15, 1993 now abandoned, which is a continuation of U.S. Ser. No. 07/740,375 filed 5 Aug. 1991, now abandoned.

BACKGROUND OF THE INVENTION

The immunosuppressive drug cyclosporin A (CsA) is an undecapeptide fungal product which has a highly specific inhibitory effect on T cell activation or differentiation in vivo and in vitro. While CsA is currently widely used to prevent allograft rejection, its utility as a therapeutic agent is also being explored in a variety of autoimmune and neoplastic conditions. The discovery and purification (Handschumacher, 1984) and ultimately the cloning of the gene encoding the most abundant intracellular receptor for CsA, cyclophilin (Haendler, 1987), promised to shed light on the mechanism of T cell inhibition by CsA.

The subsequent discovery that cyclophilin possessed an intrinsic enzymatic activity, peptidylprolyl isomerase (PPIase)(Fischer, 1989; Takahashi, 1989), and that this enzymatic activity was blocked by CsA, provided the outline for a possible explanation for the immunosuppressive action of CsA. This approach was supported by results from another immunosuppressive drug-receptor system when the receptor for FK506, the FK binding protein (FKBP), was found also to possess PPIase activity (Harding, 1989; Siekierka, 1989) that was inhibited by FK506 (see U.S. Ser. No. 07/740,175, filed 5 Aug. 1991, (now abandoned) incorporated herein by reference). However, this proposal suffered on two counts: (1) cyclophilin is expressed ubiquitously, but its main actions in vivo are highly tissue restricted; and (2) CsA congeners reveal a dissociation between inhibition of PPIase activity and immunosuppressive potency (Sigal, 1991).

SUMMARY OF THE INVENTION

The cloning of a third mammalian cyclophilin, cyp C, isolated from a cDNA library prepared from the murine bone marrow derived stromal cell line AC 6 (Whitlock, 1987), is provided. This cDNA was isolated from a subtracted sub-library containing genes induced by treatment of the stromal cell line with interleukin-1 (IL-1). The message levels for cyp C show a 2-3 fold induction by treatment with IL-1, and this cDNA exhibits a high level of homology with known cyclophilins.

Cyp C is a mediator for the immunosuppressive and nephrotoxic actions of CsA, as it is expressed most highly in the kidney, and can be detected in activated T cells as well as in the bone marrow stromal line AC 6. Cyp C can also be used as an affinity probe for cytoplasmic proteins involved in its functions in the absence (presumably related to PPIase) or presence (presumably signal transduction inhibition) of CsA; in the absence of CsA the main partner is a 77Kd protein, while in the presence of CsA the CsA:cyp C complex no longer binds the p77, but now binds a novel p55 species. In a patent application filed on 5 Aug. 1991, U.S. Ser. No. 07/740,175, which is incorporated herein by reference, the p55 species is identified as a calcineurin, which is involved in signal transduction associated events that are blocked by CsA and FK506.

Also provided are homologs and binding fragments to the cyp C polypeptide family, as well as methods for producing the peptide desired. Antibodies capable of specifically binding the cyp C polypeptide or binding fragment thereof are also provided. In addition, this invention includes a substantially-pure complex comprising a cyclophilin C polypeptide, and a protein having a molecular weight of about 77Kd as identified by SDS-PAGE. This 77Kd binds to a cyclophilin C polypeptide in the absence of cyclosporin A, which binding is not calcium dependent.

BRIEF DESCRIPTION OF THE FIGURES

FIGS. 1—1 and 1-2. Nucleotide and presumed amino acid sequence of cyp C mRNA (SEQ. ID pos: 4 and 5). Cyp C mRNA was isolated from a subtracted cDNA library containing genes expressed by the AC 6 cell line upon induction by IL-1. The length of this cDNA (1288 bp) corresponds well with the observed size of the poly-A containing cyp C message (~1400 bp).

FIGS. 2-1 and 2—2. Amino acid sequence alignment comparing the two forms of yeast cyclophilin, yeast 1 (Haendler, 1989) and yeast 2 (Koser, 1990), with murine cyp C, human cyp B (Price, 1991) and murine cyp A (Hasel, 1990(SEQ. ID NOS: 5-9)). Residues absolutely conserved among all sequences are boxed and shown in bold face. Homologous residues in adjacent sequence are indicated by a vertical line.

In FIG. 8A the interaction of cyp C with the 77Kd protein in the absence of CsA is shown. In FIG. 8B the interaction of cyp C with the 55Kd protein in the presence of CsA is shown.

DETAILED DESCRIPTION OF THE INVENTION

A new mammalian cyclophilin, cyp C, has been isolated from a bone marrow derived stromal cell line. Cyp C is distinct from mammalian cyclophilins A and B in both sequence and tissue distribution of expression. Cyp C possesses peptidyl-prolyl isomerase (PPIase) activity, and this activity can be completely inhibited by addition of CsA. A cyp C-GST fusion protein was used as an affinity ligand to identify cellular proteins of 77Kd and 55Kd which bind specifically to cyp C respectively in the absence or presence of CsA. While the exact relationship between the 55Kd protein and the 77Kd protein remains to be elucidated, cell lysates depleted of 77Kd protein still contain the same amount of 55Kd protein as control samples. In addition, there is no apparent functional relationship between p55 and p77. It seems more likely that cyp C:p77 represents one functional complex, and CsA:cyp C:p55 represents another. In that view, understanding the function of p55 alone or in the CsA:cyp C:p55 complex could reveal the immunosuppressive function of CsA, while identifying the structure and function of p77 might lead to an understanding of the normal function of (at least) the cyp C PPIase.

Currently, there is no widely accepted model which explains the immunosuppressive effects of CsA and the functionally similar macrolide FK506 (see U.S. Ser. No. 07/740,175, filed 5 Aug. 1991, incorporated herein by reference) Each drug is a naturally occurring fungal product which binds specifically to a class of proteins termed immunophilins (Bierer, 1990; Schreiber, 1991). While all immunophilins thus far isolated are prolylisomerases in their free form, the cognate drug:immunophilin complexes (CsA for cyclophilins, FK506 and rapamycin for the FKBP's) (see U.S. Ser. No. 07/740,175, filed 5 Aug. 1991, incorporated herein by reference) lack that activity. The mechanism(s) by which these immunosuppressive ligands inhibit T cell signal transduction is unknown, as is the normal function(s) of the immunophilins in T cells and other tissues in which they are expressed. Current evidence suggests that CsA and FK506 possess virtually identical bioactivities, blocking T cell activation by interfering with an intracellular signaling event distal to both calcium flux and phosphatidyl inositol hydrolysis (Dumont, 1.990; Tocci, 1989). The nature of this signaling event is poorly understood, but evidence has been presented that CsA specifically inhibits the function of nuclear proteins involved in T cell activation, especially the transcriptional activator NF-AT (Emmel, 1989), though there is no evidence that CsA interacts directly with transcriptional activators. Here it has been demonstrated that a new member of the cyclophilin family, cyp C, can be used as an affinity reagent to specifically isolate cellular proteins that could be involved in these mechanisms.

Figure 8A:
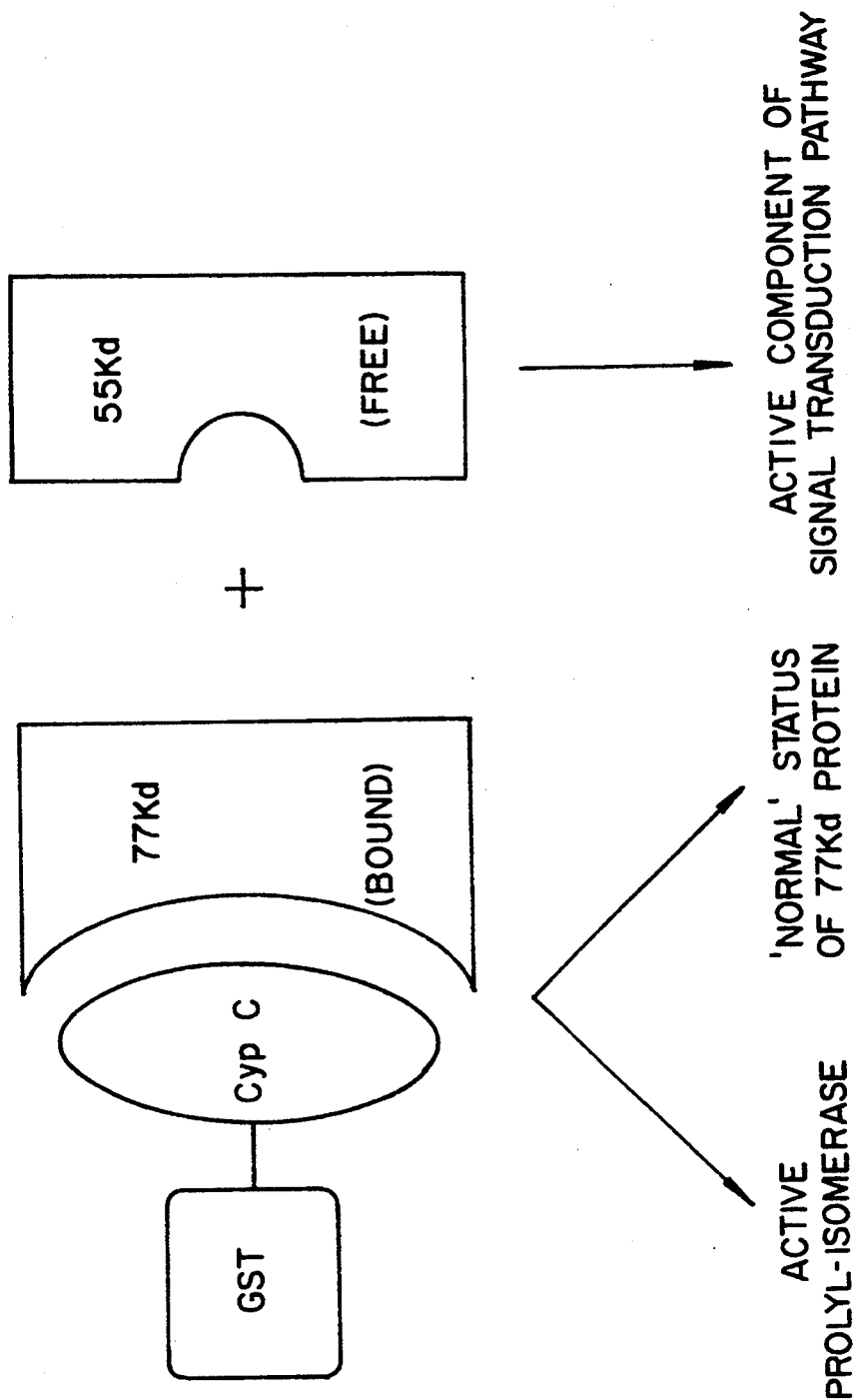
FIGS. 8A and 8B. Schematic model of the observed interactions of cyp C and intracellular proteins, and the alteration of these interactions by the introduction of CsA.
Figure 8B:
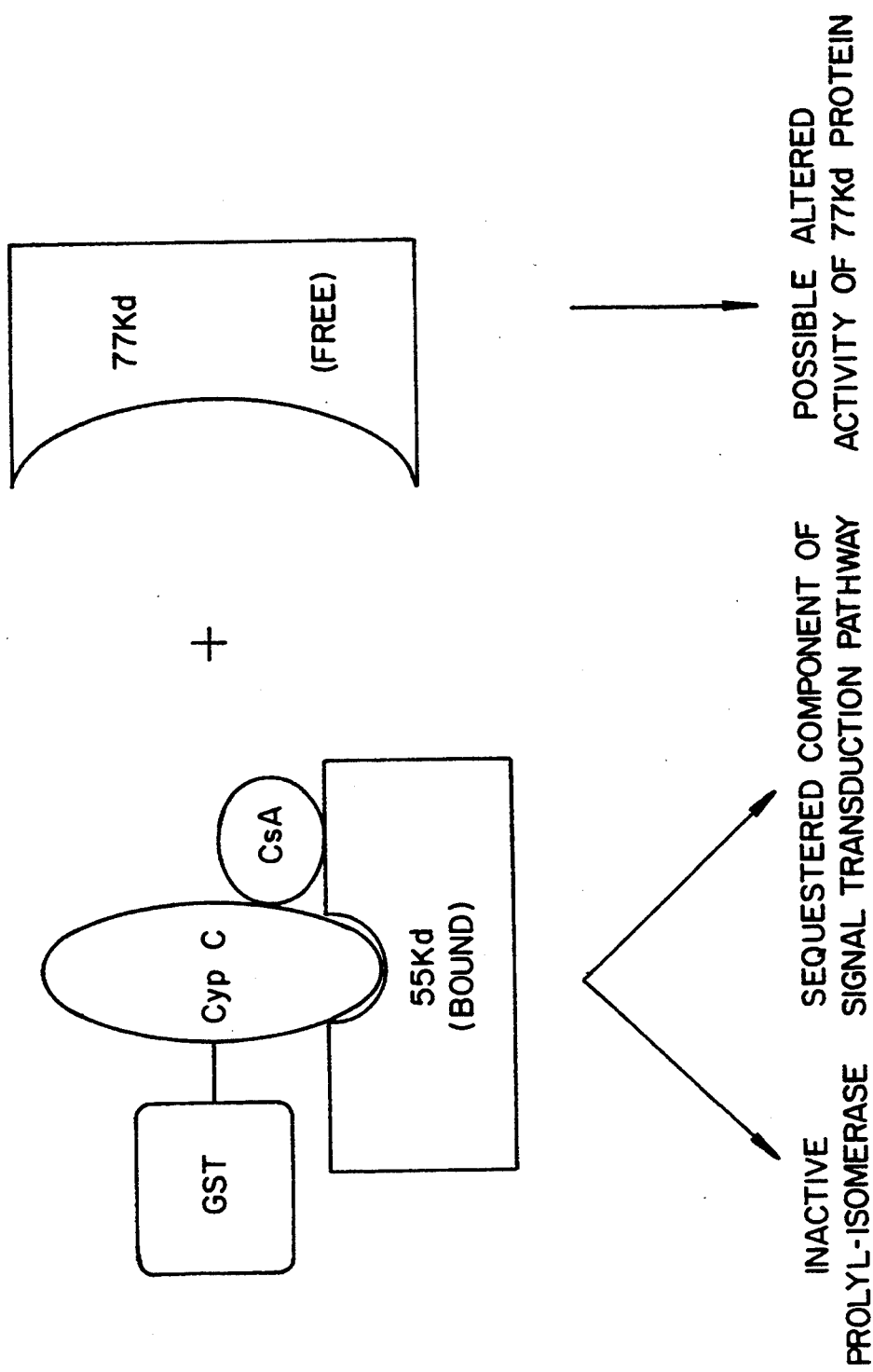

In FIGS. 8A and 8B a model of the observed protein interactions with cyp C in the presence and absence of CsA is presented. In light of the high affinity of the interactions observed, a high fraction of the 77Kd protein in contact with native cyp C is proposed to exist in a bound conformation, assuming that both are present in the same subcellular compartment. The addition of CsA to cell lysate preparations results in the elution of the 77Kd protein from the cyp C fusion protein. This is likely to occur also in intact cells. Upon binding CsA, cyp C becomes a high affinity ligand for the 55Kd protein. In intact cells, CsA binding is presumably followed by drug:receptor complexes binding to accessible free 55Kd protein. The sequestration of the 55Kd protein into drug:receptor complexes and the potential alteration of its normal function is likely to be a key to understanding the mechanism of action of CsA, while it is still a formal possibility that the release of the 77Kd protein from a normally bound conformation is the physiologically important event at the drug:receptor interface. However, the results of the titration experiment (FIG. 6) suggest that at pharmacologically relevant concentrations of CsA, significant amounts of the 55Kd protein may be sequestered in drug:receptor complexes, while the pool of 77Kd protein should be relatively unaffected. The 77Kd protein is apparently intimately involved in the normal function of cyp C, perhaps related to its isomerase activity. The 55Kd protein is also recognized by the FK506:FKBP complex, and is itself a likely candidate for a critical step in a signal transduction pathway.

Figure 3:
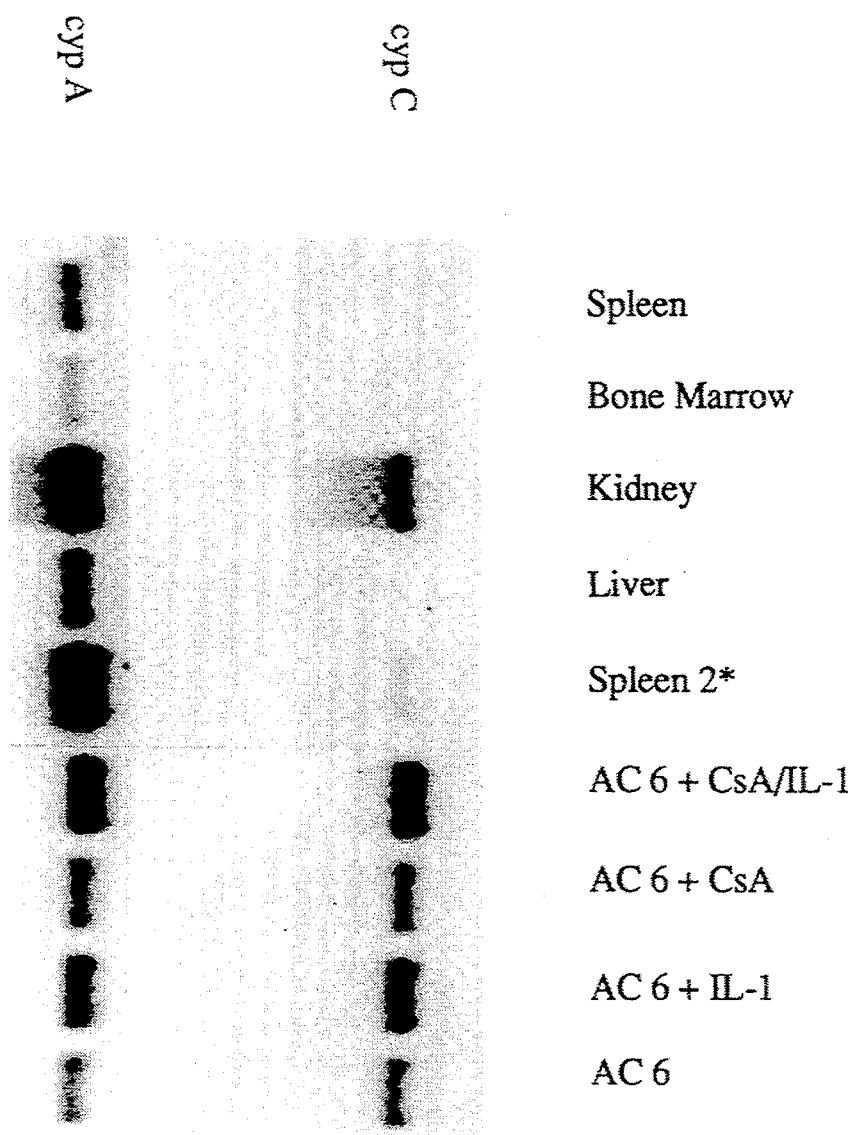
FIG. 3. Northern analysis of cyp C and cyclophilin A mRNA's. Twenty micrograms (20 $\mu$g) of total tissue or cell line RNA were loaded per lane and probed with cyp C or cyclophilin A sequences as described below. The cyp C mRNA is approximately 1400 bases, while the cyp A mRNA is approximately 1000 bases. The spleen 2* sample is RNA prepared from the spleen of an animal undergoing hematopoietic reconstitution. This spleen contained numerous colony forming units (CFUs) (day 12), and was a source of rapidly dividing immature myeloid and erythroid cells.

Cyp C was isolated from a cDNA library prepared from the murine bone marrow derived stromal cell line AC 6. A subtractive hybridization strategy was used to isolate genes induced by IL-1, and cyp C as well as cyp A fall within this group (FIG. 3). Cyp C and cyp A mRNAs both are elevated approximately three-fold in AC 6 cells in response to induction by IL-1 (FIG. 3). As expected, no effect of CsA was detected on the expression of cyp C in AC 6 cells. Bone marrow stromal cells such as AC 6 cells are known to secrete a variety of hemopoietic growth factors and regulators, both constitutively and after induction by IL-1 (Lovhaug, 1986).

Sequence comparisons between cyp C and other cyclophilins (FIGS. 2-1 and 2—2) demonstrate that cyp C shares between 50% and 77% identity in a core homology region (residues 36–205 of cyp C) with other cyclophilins. Outside of this region, the amino terminus is unique in sequence, but similar in its overall size to the amino termini of human cyp B, drosophila ninaA, and the larger cyclophilins isolated from neurospora and saccharomyces. The carboxyl terminus is also unique in sequence, but there is evident homology with the carboxyl termini of human cyp B and yeast cyp 2. While cyp A proteins are thought to be free in the cytosol, the cellular localization of cyp B, cyp C and yeast cyp 2 is currently unknown. Each protein contains an amino-terminal extension of 33–35 amino acids rich in nonpolar residues, relative to cyp A or yeast cyp 1. The amino terminal region of cyp B can act as a signal sequence when expressed in *E. coli* (Price, 1991), raising the possibility that these cyclophilins may reside within membrane bound organelles, and/or associated with the plasma membrane, or possibly even be secreted. Recently, the Drosophila cyclophilin homologue ninaA has been shown to be an integral membrane protein with a C-terminal anchor and a cleavable signal sequence (Stamnes, 1991). The phenotype of the ninaA mutation is a dramatic reduction in the Rh1 rhodopsin content of specific photoreceptor cells. This reduction in Rh1 rhodopsin is due to a post-transcriptional defect, presumably in the processing of the rhodopsin molecule. The implied function of the ninaA cyclophilin homologue is the isomerization about an Xaa-prolyl bond in Rh1 rhodopsin, allowing for the proper processing of the molecule. The apparent selectivity of this interaction raises the possibility that there exist a profusion of cyclophilins tailored to the processing, folding, translocation or other requirements of specific cellular proteins.

Also identified is a cellular protein of 77Kd which interacts specifically with cyp C. By analogy with the ninaA/rhodopsin system, this 77Kd protein is likely to be a major substrate for the cyp C PPIase activity, it may aid cyp C in its normal function, perhaps serving as a chaperone molecule akin to a heat shock protein for cyp C substrates, or it may represent a natural inhibitor (endogenous CsA agonist or antagonist) of the activity of cyp C, among other possibilities. Alternatively, as the cyp C:CsA complex intersects and is likely to block a signal transduction pathway, the cyp C:77Kd complex may also be part of a signaling pathway.

The role of immunophilin PPIase activity in immunosuppression has been challenged by a number of experiments. Studies with analogues of CsA (Durette, 1988; Sigal, 1991) demonstrate that some compounds have the ability to inhibit the PPIase activity of cyclophilin A, but lack immunosuppressive activity, while others are relatively poor inhibitors of PPIase, but retain immunosuppressive action. Similar results have been obtained in the FKBP/FK506 system (see U.S. Ser. No. 07/740,175, filed 5 Aug. 1991, now abandoned) using a nonnatural immunophilin ligand, 506BD, which is an efficient inhibitor of the FKBP rotamase, has no effect on T cell activation, and is able to block the immunosuppressive effects of both FK506 and rapamycin (Bierer, 1990). Assuming the immunosuppressive effects of immunophilin:drug complexes are unrelated to inhibition of isomerase function, the likely means of the observed blockade of signal transduction is the 55Kd protein, calcineurin (see U.S. Ser. No. 07/740,175, filed 5 Aug. 1991), especially because it also is bound to a FKBP:FK506 affinity matrix. Immunophilins also may serve as convenient substrates to which a bifunctional ligand (e.g., CsA, FK506) 'glues' a third molecule such as the calcineurin protein (see U.S. Ser. No. 07/740,175, filed 5 Aug. 1991). The immunosuppressive ligands CsA and FK506 (see U.S. Ser. No. 07/740,175, filed 5 Aug. 1991) reveal a potential role of the immunophilins in signal transduction. It is conceivable that endogenous molecules akin to CsA and FK506 (see U.S. Ser. No. 07/740,175, filed 5 Aug. 1991) are normally present in cells, and that these molecules regulate signal transduction pathways through interaction with the immunophilins. Studies of the 77Kd molecule identified here help to clarify the normal role of the immunophilins in signal transduction and protein processing.

A possible explanation for the results of studies with analogues of CsA includes the presence of other CsA receptors in the cell, perhaps with higher affinity or important subcellular localization. In Neurospora and Saccharomyces, CsA may exert its effect by forming a toxic 'complex' with its receptor(s) and other as yet unidentified cellular components (Tropschug, 1989). By analogy, such a complex may be responsible for the inhibition of T cell activation, and the nephrotoxicity observed in mammals. These results support the notion that it is the association of the CsA:cyp C complex with the 55Kd protein that results in the CsA effects observed.

The isolation of additional mammalian CsA binding proteins calls into question the role of cyclophilin A as the physiologically important CsA binding protein. Cyclophilin A is apparently ubiquitously expressed at relatively high levels (0.05 to 0.4% of total cytoplasmic protein) (Koletsky, 1986), though the effects of CsA seem restricted to T lymphocytes, renal and neural tissues as evidenced by immunologic effects and clinical toxicity. The tissue distribution of expression of cyp C is interesting as the message is produced at relatively high levels in the kidney, and the kidney is known to be susceptible to progressive damage during the course of CsA therapy. In situ hybridization of adult mouse kidney with antisense cyp C $^{35}$S labelled probes reveals a very specific distribution of expression, namely the cortico-medullary junction. Cyp C mRNA is also present in a variety of murine T and B cell lines, but is not detectable by northern analysis in total thymic RNA. Thus, cyp C expression in lymphocytes may be regulated by their state of activation. Understanding the functional role of the 77Kd and 55Kd proteins and other associating proteins isolated from specific tissues could provide information relevant to the activity of CsA on T cell mediated immunity, nephrotoxicity and other tissue specific effects of CsA such as mast cell degranulation (Hultsch, 1990).

In summary, cyclophilin C is a new member of the mammalian cyclophilin family. It is highly homologous to all previously isolated cyclophilins, demonstrates a tissue-specific expression pattern, and possesses unique amino and carboxy terminal sequences. cyp C is active as a prolyl-isomerase, and can be inhibited by CsA. Cyp C demonstrates highly specific interactions with cellular proteins, both in the presence and absence of CsA. In the absence of CsA, cyp C binds to a 77Kd protein which can be found in a variety of cell types. In the presence of CsA, cyp C binds to a 55Kd protein identified as calcineurin (see U.S. Ser. No. 07/740,175, filed 5 Aug. 1991, now abandoned), which can also be found in a variety of cell types. Both protein interactions occur across a murine:human species barrier, underscoring the evolutionary conservation of both the protein components and their domains for interaction. The observation that the 55Kd protein is also bound by FKBP:FK506 affinity matrices and its identification as a possible candidate in a signal transduction pathway furthers understanding of the mechanism of action of CsA and FK506 (see U.S. Ser. No. 07/740,175, filed 5 Aug. 1991).

This invention includes the binding protein class of cyclophilin C polypeptides. Also included are homologous sequences, allelic variations, natural mutants, induced mutants, alternatively expressed variants, and proteins encoded by DNA which hybridize under high or low stringency conditions, to cyp C encoding nucleic acids retrieved from naturally occurring material. Closely related cyp C-like polypeptides or proteins retrieved by antisera to cyp C are also included.

The present invention also provides for other polypeptides comprising binding fragments of cyp C polypeptides substantially homologous thereto. The receptor peptides of the present invention will generally exhibit at least about 80% homology with naturally occurring sequences, typically at least about 85% homology with a natural cyp C sequence, more typically at least about 90% homology, usually at least about 95% homology, and more usually at least about 97% homology. The length of comparison sequences will generally be at least about 16 amino acids, usually at least about 20 residues, more usually at least about 24 residues, typically at least about 28 residues, and preferably more than about 35 residues.

Homology, for polypeptides, is typically measured using sequence analysis software, see, e.g., Sequence Analysis Software Package of the Genetics Computer Group, University of Wisconsin Biotechnology Center, 1710 University Avenue, Madison, Wis. 53705. Protein analysis software matches similar sequences using measure of homology assigned to various substitutions, deletions, substitutions, and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

As used herein, the terms substantially pure and homogenous describe a protein or polypeptide which has been separated from components which naturally accompany it. Typically, a monomeric protein is substantially pure when at least about 60 to 75% of a sample exhibits a single polypeptide backbone. Minor variants or chemical modifications typically share the same polypeptide sequence. A substantially pure protein will typically comprise over about 85 to 90% of a protein sample, more usually will comprise at least about 95%, and preferably will be over about 99% pure. Normally, purity is measured on a polyacrylamide gel, with homogeneity determined by staining. For certain purposes high resolution will be used and HPLC or a similar means for purification utilized. For most purposes, a simple chromatography column or polyacrylamide gel will be used to determine purity.

A protein is substantially free of naturally associated components when it is separated from the native contaminants which accompany it in its natural state. Thus, a protein which is chemically synthesized or synthesized in a cellular system different from the cell from which it naturally originates will be substantially free from its naturally associated components. The term is used to describe polypeptides and nucleic acids which have been synthesized in heterologous mammalian cells or plant cells, E. coli and other prokaryotes.

The present invention provides for substantially pure preparations. Various methods for their isolation from biological material may be devised, based in part upon the structural and functional descriptions contained herein. Depending on the availability of specific antibodies, as provided herein, specific cyp C polypeptides may also be purified using immunoaffinity chromatography. Antibodies prepared as described below, may be immobilized to an inert substance to generate a highly specific affinity column. Various cell or tissue sources may be selected as starting materials usually selected due to an abundance of the desired proteins, such as those described in the examples below.

To determine the amino acid sequence or to obtain polypeptide fragments of cyp C, the protein may be digested with trypsin. Peptide fragments may be separated by reversed-phase high performance liquid chromatography (HPLC) and analyzed by gas-phase sequencing. Other sequencing methods known in the art may also be used. The cyp C poly peptides or specific regions of the cyp C family may be used to affinity purify respective members.

A signal or leader sequence can direct the cyp C protein through the membrane of a cell. Therefore the appropriate signal sequence may be used in conjunction with the protein.

The present invention also provides for analogues of the cyp C polypeptides. Such analogues include both modifications to a polypeptide backbone and variants and mutants of the polypeptides. Modifications include chemical derivatizations of polypeptides, such as acetylations, carboxylations and the like. They also include glycosylation modifications and processing variants of a typical polypeptide. These processing steps specifically include enzymatic modifications, such as ubiquinization. See, e.g., Hershko and Ciechanover (1982), "Mechanisms of Intracellular Protein Breakdown," *Ann. Rev. Bioch.*, 51:335–364.

In particular, glycosylation alterations are included, made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Also embraced are versions of the same primary amino acid sequence which have phosphorylated amino acid residues, e.g., phosphotyrosine, phosphoserine, or phosphothreonine.

Other analogues include genetic variants, both natural and induced. Induced mutants may be derived from various techniques including both random mutagenesis of the encoding nucleic acids using irradiation or exposure to EMS, or may take the form of engineered changes by site-specific mutagenesis or other techniques of modern molecular biology. See, Sambrook, Fritsch and Maniatis (1989), *Molecular Cloning: A Laboratory Manual* (2d ed.), CSH Press.

Besides substantially full-length polypeptides, the present invention provides for biologically active fragments of the polypeptides. Significant biological activities include ligand-binding, immunological activity and other biological activities characteristic of cyp C polypeptides. Immunological activities include both immunogenic function in a target immune system, as well as sharing of immunological epitopes for binding, serving as either a competitor or substitute antigen for a cyp C epitope. As used herein, the term fragment or segment, as applied to a polypeptide, will ordinarily be at least about 5 contiguous amino acids, typically at least about 7 contiguous amino acids, more typically at least about 9 contiguous amino acids, usually at least about 11 contiguous amino acids, preferably at least about 13 contiguous amino acids, more preferably at least about 16 contiguous amino acids, and most preferably at least about 20 to 30 or more contiguous amino acids. Segments of a particular domain will be segments of the appropriate size within the corresponding domain.

For immunological purposes, immunogens may be produced which tandemly repeat polypeptide segments, thereby producing highly antigenic proteins. Alternatively, such polypeptides will serve as highly efficient competitors for specific binding. Production of antibodies to cyc C polypeptides or fragments is described below.

The present invention also provides for other polypeptides comprising fragments of cyp C polypeptides. Thus, fusion polypeptides between the cyp C polypeptides and other homologous or heterologous proteins are provided. Homologous polypeptides may be fusions between different cyclophilins, resulting in, for instance, a hybrid protein, or a fusion protein which may have broadened or weakened specificity of binding. Likewise, heterologous fusions may be constructed which would exhibit a combination of properties or activities of the derivative proteins. For example, ligand-binding or other domains may be "swapped" between different new fusion polypeptides or fragments. Thus, new chimeric polypeptides exhibiting new combinations of specificities result from the functional linkage of ligand-binding specificities and intracellular domains. For example, the Ig domains may be substituted by Ig domains from other related polypeptides. Other gene fusion partners include bacterial $\beta$-galactosidase, trpE Protein A, $\beta$-lactamase, alpha amylase, alcohol dehydrogenase and yeast alpha mating factor. See, e.g., Godowski et al. (1988), *Science* 241:812–816.

Fusion proteins will typically be made by either recombinant nucleic acid methods or by synthetic polypeptide methods. Techniques for nucleic acid manipulation are described generally, for example, in Sambrook et al. (1989), *Molecular Cloning: A Laboratory Manual* (2d ed.), Vols. 1-3, Cold Spring Harbor Laboratory. Techniques for synthesis of polypeptides are described, for example, in Merrifield, *J. Amer. Chem. Soc.* 85:2149–2156 (1963). The recombinant nucleic acid sequences used to produce fusion proteins of the present invention may be derived from natural or synthetic sequences. Many natural gene sequences are obtainable from various cDNA or from genomic libraries using appropriate probes. See, GenBank TM, National Institutes of Health. Suitable synthetic DNA fragments may be prepared by the phosphoramidite method described by Beaucage and Carruthers, *Tetra. Letts.* 22:1859–1862 (1981). A double-stranded fragment may then be obtained either by synthesizing the complementary strand and annealing the strand together under appropriate conditions or by adding the complementary strand using DNA polymerase with an appropriate primer sequence.

The present invention provides nucleic acid sequences encoding cyp C polypeptide sequences described above. Nucleic acids according to the present invention will possess a sequence which is either derived from a natural source gene or one having substantial homology with a natural cyp C gene or a portion thereof.

Substantial homology in the nucleic acid context means either that the segments, or their complementary strands, when optimally aligned and compared, are identical with appropriate nucleotide insertions or deletions, in at least about 80% of the residues, usually at least about 90%, more usually at least about 95%, preferably at least about 97%, and more preferably at least about 98 to 99.5% of the nucleotides. Alternatively, substantial homology exists when the segments will hybridize under selective hybridization conditions, to a strand, or its complement. Selectivity of hybridization exists when hybridization occurs which is more selective than total lack of specificity. Typically, selective hybridization will occur when there is at least about 55% homology over a stretch of at least about 14/25 nucleotides, preferably at least about 65%, more preferably at least about 75%, and most preferably at least about 90%. See, Kanehisa, M. (1984), *Nucleic Acids Res.* 12:203–213, which is incorporated herein by reference. Stringent hybridization conditions will typically include salt concentrations of less than about 1M, more usually less than about 500 mM and preferably less than about 200 mM. Temperature conditions will typically be greater than 20° C., more usually greater than about 30° C. and preferably in excess of about 37° C. As other factors may significantly affect the stringency of hybridization, including, among others, base composition and size of the complementary strands, presence of organic solvents and extent of base mismatching, the combination of parameters is more important than the absolute measure of any one.

An "isolated" nucleic acid is a nucleic acid, e.g., an RNA, DNA, or a mixed polymer, which is substantially separated from other DNA sequences which naturally accompany a native human sequence, e.g., ribosomes, polymerases, and many other human genome sequences. The term embraces a nucleic acid sequence which has been removed from its naturally occurring environment, and includes recombinant or cloned DNA isolates and chemically synthesized analogues or analogues biologically synthesized by heterologous systems. A substantially pure molecule includes isolated forms of the molecule.

An isolated nucleic acid will generally be a homogenous composition of molecules, but will, in some embodiments, contain minor heterogeneity. This heterogeneity is typically found at the polymer ends or portions not critical to a desired biological function or activity.

The term "encoding" refers generally to the sequence information being present in a translatable form, usually operably linked to a promoter. A sequence is operably linked to a promoter when the functional promoter enhances transcription or expression of that sequence. An anti-sense strand is considered to also encode the sequence, since the same informational content is present in a readily accessible form, especially when linked to a sequence which promotes expression of the sense strand. The information is convertible using the standard, or a modified, genetic code. See, e.g., Watson et al. (1987) *The Molecular Biology of the Gene* (4th ed.) vols. 1&2, Benjamin, Menlo Park, Calif.

The term "recombinant" refers to a nucleic acid sequence which is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the common natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide.

Homologous sequences, when compared, exhibit similarity. The standards for homology in nucleic acids are either measures for homology generally used in the art or hybridization conditions. Substantial homology in the nucleic acid context means either that the segments, or their complementary strands, when compared, are identical when optimally aligned, with appropriate nucleotide insertions or deletions, in at least about 60% of the residues, usually at least about 70%, more usually at least about 80%, preferably at least about 90%, and more preferably at least about 95 to 98% of the nucleotides. Alternatively, substantial homology exists when the segments will hybridize under selective hybridization conditions, to a strand, or its complement. Selectivity of hybridization exists when hybridization occurs which is more selective than total lack of specificity. Typically, selective hybridization will occur when there is at least about 55% homology over a stretch of at least about 14 nucleotides, preferably at least about 65%, more preferably at least about 75%, and most preferably at least about 90%. See, Kanehisa (1984) *Nuc. Acids Res.* 12:203-213, which is incorporated herein by reference. The length of homology comparison, as described, may be over longer stretches, and in certain embodiments will often be over a stretch of at least about 17 nucleotides, usually at least about 20 nucleotides, more usually at least about 24 nucleotides, typically at least about 28 nucleotides, more typically at least about 32 nucleotides, and preferably at least about 36 or more nucleotides.

Stringent conditions, in referring to homology, will be stringent combined conditions of salt, temperature, organic solvents, and other parameters typically controlled in hybridization reactions. Stringent temperature conditions will generally include temperatures in excess of 30° C., typically in excess of 37°, and preferably in excess of 45°. Stringent salt conditions will ordinarily be less than 1000 mM, typically less than 500 mM, and preferably less than 200 mM. However, the combination of parameters is much more important than the measure of any single parameter. See, e.g., Wetmur and Davidson (1968) *J. Mol. Biol.* 31:349-370, which is hereby incorporated herein by reference.

Probes may be prepared based on the sequence of the cyp C cDNAs provided. The probes will include an isolated nucleic acid attached to a label or reporter molecule and may be used to isolate other cyp C nucleic acid sequences by standard methods. See, e.g., J. Sambrook et al., *Molecular Cloning: A Laboratory Manual*, Vols. 1-3, CSH Press, N.Y. (1989), which is hereby incorporated herein by reference. Other similar nucleic acids may be selected by using homologous nucleic acids. Alternatively, nucleic acids encoding these same or similar polypeptides may be synthesized or selected by making use of the redundancy in the genetic code. Various codon substitutions may be introduced, e.g., silent changes thereby producing various restriction sites, or to optimize expression for a particular system. Mutations may be introduced to modify the properties of the polypeptide receptors, perhaps to change the ligand-binding affinities, the interchain affinities, or the polypeptide degradation or turnover rate.

The DNA compositions of this invention may be derived from genomic DNA or cDNA, prepared by synthesis or may be a hybrid of the various combinations. Recombinant nucleic acids comprising sequences otherwise not naturally occurring are also provided by this invention. An isolated DNA sequence includes any sequence that has been obtained by primer or hybridization reactions or subjected to treatment with restriction enzymes or the like.

Synthetic oligonucleotides can be formulated by the triester method according to Matteucci, et al., *J. Am. Chem. Soc.*, 103:3185 (1981) or by other methods such as commercial automated oligonucleotide synthesizers. Probes may also be prepared by nick translation, Klenow fill-in reaction, or other methods known in the art. cDNA or genomic libraries of various types may be screened. The choice of cDNA libraries normally corresponds to a tissue source which is abundant in mRNA for the desired receptors. Phage libraries are normally preferred, but plasmid libraries may also be used. Clones of a library are spread onto plates, transferred to a substrate for screening, denatured and probed for the presence of desired sequences.

In accordance with this invention any isolated DNA sequence which encodes a cyp C structural sequence can be used as a probe. Any isolated partial DNA sequence which encodes a cyp C activity is also part of this invention.

The DNA sequences used in this invention will usually comprise at least about 5 codons (15 nucleotides), more usually at least about 7 codons, typically at least about 10 codons, preferably at least about 15 codons, more preferably at least about 25 codons and most preferably at least about 35 codons. One or more introns may also be present. This number of nucleotides is usually about the minimal length required for a successful probe that would hybridize specifically with an a cyp C polypeptide. For example, epitopes characteristic of a cyp C may be encoded in short peptides. Usually the wild-type sequence will be employed, in some instances one or more mutations may be introduced, such as deletions, substitutions, insertions or inversions resulting in changes in the amino acid sequence to provide silent mutations, to modify a restriction site, or to provide specific mutations. The genomic sequence will usually not exceed about 200 kb, more usually not exceed about 100 kb, preferably not greater than 5.0 kb.

Portions of the DNA sequence having at least about 15 nucleotides, usually at least about 15 nucleotides, and fewer than about 6 kb, usually fewer than about 1.0 kb, from a DNA sequence encoding cyp C are preferred as probes. The probes may also be used to determine whether mRNA encoding a specific cyp C is present in a cell or different tissues.

The natural or synthetic DNA fragments coding for a desired fragment will be incorporated into DNA constructs capable of introduction to and expression in an in vitro cell culture. Usually the DNA constructs will be suitable for replication in a unicellular host, such as yeast or bacteria, but may also be intended for introduction to, with and without and integration within the genome, cultured mammalian or plant or other eukaryotic cell lines. DNA constructs prepared for introduction into bacteria or yeast will typically include a replication system recognized by the host, the intended DNA fragment encoding the desired receptor polypeptide, transcription and translational initiation regulatory sequences operably linked to the polypeptide encoding segment and transcriptional and translational termination regulatory sequences operably linked to the polypeptide encoding segment. The transcriptional regulatory sequences will typically include a heterologous enhancer or promoter which is recognized by the host. The selection of an appropriate promoter will depend upon the host, but promoters such as the trp, lac and phage promoters, tRNA promoters and glycolytic enzyme promoters are known. See, Sambrook et al., *Molecular Cloning: A Laboratory Manual* (2d ed.), CSH Press (1989). Conveniently available expression vectors, which include the replication system and transcriptional and translational regulatory sequences together with the insertion site for the cyp C polypeptide DNA sequence, may be employed. Examples of workable combinations of cell lines and expression vectors are described in Sambrook et al. (1989); see also, Metzger et al. (1988), *Nature* 334:31-36.

Expression vectors for these cells can include expression control sequences, such as an origin of replication, a promoter, an enhancer and necessary processing information sites, such as ribosome-binding sites, RNA splice sites, polyadenylation sites, and transcriptional terminator sequences. Preferably, the enhancers or promoters will be those naturally associated with genes encoding the cyp C polypeptides, although it will be understood that in many cases others will be equally or more appropriate.

The vectors containing the DNA segments of interest can be transferred into the host cell by well-known methods, which vary depending on the type of cellular host. For example, calcium chloride transfection is commonly utilized for procaryotic cells, whereas calcium phosphate treatment may be used for other cellular hosts. See generally, Sambrook et al. (1989). The term "transformed cell" is meant to also include the progeny of a transformed cell.

DNA sequences may also be used to express polypeptides which exhibit or inhibit cyp C activity.

Large quantities of the peptides may be prepared by expressing the whole DNA of cyp C or portions of the DNA in vectors or other expression vehicles in compatible hosts such as *E. coli*, yeast, mammalian cells, insect cells or frog oocytes. The expression vehicles may be introduced into the cells using methods well known in the art such as calcium phosphate precipitation, lipofectin, electroporation or DEAE dextran.

To study the characteristics of cyp C polypeptides, it will be useful to transfect mammalian cells which lack or have low levels of cyp C activity where the signal sequence directs the peptide to a subcellular compartment. Transformed or transfected cells will enable one to analyze the binding properties of various cyp C polypeptides. Transfected cells may also be used to evaluate a composition or drug's effectiveness as an antagonist or agonist.

Although the most common procaryote cells used as hosts are strains of *E. coli*, other procaryotes such as *Bacillus subtilis* or Pseudomonas may also be used. The DNA sequence of the invention, including fragments or portions of the sequence encoding for a cyp C polypeptide, a portion thereof or a polypeptide having cyp C activity can be used to prepare an expression vehicle or construct. Usually the control sequence will be a eukaryotic promoter for expression in a mammalian cell. A common procaryotic plasmid vector for transforming *E. coli* is pBR322 or its derivatives (e.g., the plasmid pkt279 (Clontech)) (Bolavar et al., *Gene*, 2:95 (1977)).

The procaryotic vectors may also contain procaryotic promoters for transcription initiation, optionally with an operator. Examples of most commonly used procaryotic promoters include the beta-lactamase (penicillinase) and lactose (lac) promoter (Cheng et al., *Nature*, 198:1056 (1977), the tryptophan promoter (trp) (Goeddell et al., *Nucleic Acid Res.*, 8: 457 (1980)) the $P_L$ promoter and the N-gene ribosome binding site (Shimatake et al., *Nature*, 292:128 (1981).

Promoters used in conjunction with yeast can be promoters derived from the enolase gene (Holland et al., *J. Biol. Chem.*, 256:1385 (1981)) or the promoter for the synthesis of glycolytic enzymes such as 3-phosphoglycerate kinase (Hitzeman et al., *J. Biol. Chem.*, 255 (1980)).

Appropriate nonnative mammalian promoters might include the early and late promoters from SV40 (Fiers et al., *Nature*, 273:113 (1978) or promoters derived from murine molony leukemia virus, mouse mammary tumor virus, avian sarcoma viruses, adenovirus II, bovine papilloma virus or polyoma. In addition, the construct may be joined to an amplifiable gene (e.g., DHFR) so that multiple copies of the gene may be made.

Prokaryotes may be transformed by various methods, including using $CaCl_2$ (Cohen, S. N., *Proc. Natl. Acad. Sci. U.S.A.*, 69:2110 (1972)) or the RbCl method (Maniatus et al., *Molecular Cloning: A Laboratory Manual*, Cold Spring Harbor Press 1982)). Yeast may be transformed using a method described by Van Solingen et al., *J. Bacter.*, 130:946 (1977) and C. L. Hsiao et al., *Proc. Natl. Acad. Sci. U.S.A.*, 76:3829 (1979). With respect to eukaryotes, mammalian cells may be transfected using a calcium phosphate precipitation method described by (Graham and van der Eb, *Virology*, 52:546 (1978)), or by lipofectin (BRL) or retroviral infection (E. Gilboa, *Experimental Manipulation of Gene Expression*, Chap. 9, Academic Press P. 175 (1983)). The actual expression vectors containing appropriate sequences may be prepared according to standard techniques involving ligation and restriction enzymes (See e.g., Maniatis supra.) Commercially available restriction enzymes for cleaving specific sites of DNA may be obtained from New England BioLabs, Waltham, Mass.

Clones are selected by using markers depending on the mode of the vector construction. The marker may be on the same or a different DNA molecule, preferably the same DNA molecule. With mammalian cells the cyp C gene itself may be the best marker. In procaryotic hosts the transformant may be selected by resistance to ampicillin, tetracycline or other antibiotics. Production of a particular product based on temperature sensitivity may also serve as an appropriate marker. Various methods may be used to harvest and purify the cyp C polypeptide or peptide fragment. The peptide may be isolated from a lysate of the host. The peptide may be isolated from the cell supernatant if the peptide is secreted. The cyp C is then further purified using HPLC, electrophoresis, affinity chromatography (preferably immuno-affinity or ligand affinity).

Another method which can be used to isolate cDNA clones of cyp C related species involves the use of the polymerase chain reaction (PCR). (Saiki, R. K., et al. *Science* 230:1350 (1985). In this approach two oligonucleotides (27mers) corresponding to distinct regions of the cyp C polypeptide are synthesized and then used in the PCR reaction to amplify receptor-related mRNA transcripts from an mRNA source. Annealing of the oligonucleotides and PCR reaction condition are performed under conditions of reduced stringency. The resulting amplified fragments are subcloned, and the resulting recombinant colonies are probed with $^{32}$P-labeled full-length cyp C cDNA using both high and low stringency conditions. Clones which hybridize under low but not high stringency conditions represent related mRNA transcripts. In addition this approach can be used to isolate variant cDNA species which arise as a result of alternative splicing, see Frohman, M. A., et al., *Proc. Natl. Acad. Sci. U.S.A.*, 85:8998 (1988).

Polyclonal and/or monoclonal antibodies to the various cyp C polypeptides and binding fragments may also be prepared. The term antibody is used both to refer to a homogeneous molecular entity, or a mixture such as a serum product made up of a plurality of different molecular entities. Peptide fragments may be prepared synthetically in a peptide synthesizer and coupled to a carrier molecule (i.e., keyhole limpet hemocyanin) and injected into rabbits over several months. The rabbit serum is tested for immunoreactivity to the cyp C protein or fragment. Monoclonal antibodies may be made by injecting mice with the protein polypeptides, fusion proteins or fragments thereof. Monoclonal antibodies will be screened by ELISA and tested for specific immunoreactivity with the cyp C protein, polypeptides, or fragments thereof. See, E. Harlow and D. Lane, *Antibodies: A Laboratory Manual*, CSH Laboratories (1988), which is hereby incorporated herein by reference. These antibodies will be useful in assays as well as pharmaceuticals.

Once a sufficient quantity of the desired polypeptide has been obtained, it may be used for various purposes. A typical use is the production of antibodies specific for binding. These antibodies may be either polyclonal or monoclonal and may be produced by in vitro or in vivo techniques.

For production of polyclonal antibodies, an appropriate target immune system is selected, typically a mouse or rabbit. The substantially purified antigen is presented to the immune system in a fashion determined by methods appropriate for the animal and other parameters well known to immunologists. Typical sites for injection are in the footpads, intramuscularly, intraperitoneally, or intradermally. Of course, another species may be substituted for a mouse or rabbit.

An immunological response is usually assayed with an immunoassay. Normally such immunoassays involve some purification of a source of antigen, for example, produced by the same cells and in the same fashion as the antigen was produced. The immunoassay may be a radioimmunoassay, an enzyme-linked immunosorbent assay (ELISA), a fluorescent assay, or any of many other choices, most of which are functionally equivalent but may exhibit advantages under specific conditions.

Monoclonal antibodies with affinities of $10^8$ M$^{-1}$, preferably $10^9$ to $10^{10}$, or stronger will typically be made by standard procedures as described, e.g., in Harlow and Lane, *Antibodies: A Laboratory Manual*, CSH Laboratory (1988); or Goding, *Monoclonal Antibodies: Principles and Practice* (2d ed) Academic Press, New York (1986), which are hereby incorporated herein by reference. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter the cells are clonally separated and the supernatants of each clone are tested for their production of an appropriate antibody specific for the desired region of the antigen.

Other suitable techniques involve in vitro exposure of lymphocytes to the antigenic polypeptides or alternatively to selection of libraries of antibodies in phage or similar vectors. See, Huse et al., "Generation of a Large Combinatorial Library of the Immunoglobulin Repertoire in Phage Lambda," *Science* 246:1275–1281 (1989), hereby incorporated herein by reference. The polypeptides and antibodies of the present invention may be used with or without modification. Frequently, the polypeptides and antibodies will be labeled by joining, either covalently or noncovalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminent agents, magnetic particles and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567.

This invention is particularly useful for screening compounds by using the cyclophilin C polypeptide or binding fragment thereof in any of a variety of drug screening techniques. The advantages of using the recombinant form of the polypeptide in screening for cyclophilin C-reactive drugs include: (a) improved renewable source of the polypeptide from a specific source; and (b) subtype specificity (theoretically giving greater biological and disease specificity).

One method of drug screening utilizes eucaryotic or procaryotic host cells which are stably transformed with recombinant DNA molecules expressing the polypeptide or fragment. Such cells, either in viable of fixed form, can be used for standard receptor/ligand binding assays. Competitive assays are particularly useful, where the cells (source of cyclophilin C) are contacted and incubated with a labeled ligand having known binding affinity to the polypeptide, and a test compound whose binding affinity to the polypeptide is being measured. The bound ligand and free ligand are then separated to assess the degree of ligand binding. The amount of test compound bound is inversely proportional to the amount of labeled ligand binding measured. Any one of numerous techniques can be used to separate bound from free ligand to assess the degree of ligand binding. This separation step could typically involve a procedure such as adhesion to filters followed by washing, adhesion to plastic followed by washing, or centrifugation of the cell membranes. Viable cells could also be used to screen for the effects of drugs on cyp C mediated functions, for example, second messenger levels (Ca), proliferation, etc.

Another technique for drug screening involves an approach which provides high throughput screening for compounds having suitable binding affinity to the cyclophilin C polypeptides and is described in detail in Geysen, European Patent Application 84/03564, published on Sept. 13, 1984. First, large numbers of different small peptide test compounds are synthesized on a solid substrate such as plastic pins or some other surface. Then all the pins are reacted with the polypeptide and washed. The next step involves detecting bound polypeptide.

Purified cyclophilin C can be coated directly onto plates for use in the aforementioned drug screening techniques. However, non-neutralizing antibodies to the polypeptide can be used to capture antibodies to immobilize the cyclophilin C polypeptide on the solid phase.

This invention also contemplates the use of competitive drug screening assays where neutralizing antibodies to the polypeptide fragments compete with a test compound for binding to the cyclophilin C polypeptide. In this manner, the antibodies can be used to detect the presence of any peptide which shares one or more binding sites of cyclophilin C.

The invention will better be understood by reference to the following illustrative examples. The following examples are offered by way of illustration and not by way of limitation.

EXAMPLE 1 cDNA Cloning and Library Construction

AC 6 total RNA was prepared by the acid guanidinium thiocyanate-phenol-chloroform method (Chomczynski, 1987) and chromatographed twice on oligo-dT cellulose type III (Collaborative Research). cDNA synthesis was performed using an adaptor-primer method (Rubenstein, 1990) with slight modifications. The 41 base adaptor-primer, which had the following sequence: 5'-d(GCATGCGCGCGGCCGC-GGAGGCCTTTTTTTTTTTTTTTTTT)-3', was (SEQ. ID No. 1) the kind gift of Dr. Dan Denney. Synthesized cDNA was digested with Not 1 (New England Biolabs), and then separated on a 1.2% low melting agarose (FMC) minigel. Markers were visualized by ethidium bromide staining, and a region of the gel containing cDNA larger than ~550 base pairs was isolated. Nucleic acid was recovered by melting the gel slice at 65 degrees and chromatographing the sample over an Elutip-D column (Schliecher & Schuell) according to the manufacturer's instructions. cDNA was concentrated by ethanol precipitation and prepared for ligation into modified phagemid vectors which had been prepared by digestion with Not 1 and Eco RV as described (Rubenstein, 1990). Directional libraries were constructed in this fashion from poly A+ RNA prepared from AC 6 cells grown in the presence and absence of a $10^{-5}$ dilution of unpurified recombinant human IL-1 alpha (Dr. Steve Yanofsky, DNAX, Research Institute, Palo Alto, Calif.). Interlibrary subtraction reactions were performed as described (Rubenstein, 1990; Porteus, 1991). Two rounds of subtraction were performed before analyzing specific clones.

EXAMPLE 2

Screening of Subtracted Librarie, Sequencing and Isolation of Full Length cDNA Clone Individual bacterial colonies containing phagemid vectors which had undergone two rounds of subtraction were cultured, and plasmid miniprep DNA was prepared from them by the NaOH/SDS, NaAcetate method. cDNA inserts were isolated by digestion of the plasmid DNA with Stu 1 and Hd III followed by low-melt agarose gel electrophoresis. Inserts were visualized by UV light and excised and purified by organic extraction and precipitation for use as templates for $^{32}p$ probe synthesis. Purified inserts were labeled by random priming in the presence of 50 μCi [alpha-32P] dCTP (Amersham) and were purified by chromatography over a Sephadex G-50 column. AC 6MRNA prepared from IL-1 induced and uninduced cultures was electrophoresed on 1.0% formaldehyde-agarose gels using 0.5 μg RNA/lane as described (Sambrook, 1989). RNA was blotted onto nitrocellulose filters and prehybridized and hybridized in a solution containing 50% formamide, 6×SSC, 5×Denhardt's solution, 5 mM NaPO$_4$, 100 ug/ml sheared, denatured salmon sperm DNA, and 50 ug/ml yeast tRNA. Labeled cDNA probe, prepared as described above, was hybridized for 16 hours at 45° C. for 30 minutes, followed by washing in 0.2×SSC plus 0.1% SDS at 65° C. for 30 minutes. Filters were then placed on film for autoradiographic visualization. Clones which demonstrated clear induction upon stimulation with IL-1 were worked up by sequencing. Double-stranded DNA sequencing was performed on purified plasmid DNA with Sequenase (US Biochemical Corp.) using the dideoxy chain termination method (Sanger, 1977). The cyp C cDNA was among the first 5 differential clones sequenced.

The initial cyp C clone contained a poly-A tail and extended 5' to position 96 in the FIG. 1 sequence. The 5' end of the cyp C was obtained using a standard 30 cycle polymerase chain reaction (PCR) (Saiki, 1985), an oligonucleotide complimentary to nucleotides 470–487 (5'-CTGGGATCCGTTGGTGTC-3') (SEQ. ID NO. 2) of cyp C and an oligonucleotide complimentary to the vector just 5' of the site of cDNA insertion (5'-GTCGACGGTATCGATAAG-3'). (SEQ. ID NO. 3) PCR was performed using unsubtracted library plasmids (complexity $2 \times 10^7$ clones) as template. PCR products were digested with Bam HI and Hind II and ligated into an appropriate vector. Clones were selected for sequencing based upon the length of their Bam HI to Hind III fragments, and their ability to hybridize the 5' end of the original cDNA. Four clones were obtained and sequenced. All clones were identical to the original cDNA in the region of overlap, and were identical to each other up to their 5' termini.

Sequence alignments were generated using the Genalign program of Intelligenetics software, accessed via the Beckman Center for Molecular and Genetic Medicine computer system at Stanford University.

EXAMPLE 3

Northern Analysis of cyp C and cyp A Expression

Twenty μg of total RNA from each source was run on a 1.2% agarose formaldehyde gel and blotted onto Genescreen (DuPont) membrane. Filters were hybridized as described above for 18 hours. The final wash conditions were 0.2×SSC, 0.1% SDS at 65° C. A SacII fragment containing nucleotides 85–1288 of cyp C, and a Bam HI fragment containing the entire rat cyclophilin A cDNA (98% identical to murine cyp A) (Danielson, 1988) were labeled and purified as described above. The autoradiograms presented in the Figure represent exposures of 3 days at −70° C. with an intensifying screen for both the cyp A and the cyp C probes.

EXAMPLE 4

Preparation and Purification of Cyp C-GST Fusion Protein

The originally isolated cyp C clone extended 5' to nucleotide 96 in the FIG. 1 sequence. The original junction between vector and clone, with a Hind III site in the vector in bold, and cyp C sequences in italics. This clone was digested with Hind III and Stu I (which cuts just 3' of the poly-A tail), and the Hind III overhand was filled in. The resulting 1200 bp fragment was isolated by low melting agarose gel electrophoresis. The bacterial expression vector pGEX-2T was prepared by digestion with Eco RI followed by filling in of the overhanging ends and phosphatase treatment. The cDNA fragment and vector were ligated together using T4 DNA ligase (New England Biolabs) and transformed into *E. coli* MC1061 by electroporation. Individual bacterial clones were tested for production of fusion protein by culturing in the presence of 1 mM IPTG for 4 hours. Twenty μl of bacterial culture were pelleted in a microfuge tube, and resuspended in 25 μl of SDS-PAGE sample buffer. Samples were boiled 5 minutes and loaded on 10% SDS-PAGE gels (Laemmli, 1970) for analysis. A positive clone was selected, and a large scale preparation of cyp C fusion protein was prepared by diluting a fresh overnight culture 1:25 into 500 ml of L broth supplemented with 100 μg/ml carbenicillin. Upon reaching an $OD_{600}$ of between 0.6 and 1.0, IPTG was added to 1 mM. Cultures were continued for 4 hours after induction by IPTG, whereupon the cells were placed on ice for 30 minutes and then pelleted at 5000×g for 20 minutes. Cells were washed 1×in cold PBS, and the resuspended in cold bacterial lysis buffer (1% glucose, 25 mM Tris-HCl pH 8.0, 10 mM EDTA) with 50 ug/ml lysozyme, and left on ice overnight. Lysis was performed by passing the bacteria twice through a French press at a pressure of approximately 10,000 psi. Debris and unlysed cells were pelleted at 10,000×g for 10 minutes at 4° C. Supernatant containing soluble fusion protein was incubated with 10 ml of a 50% solution of glutathione agarose (glu-ag) (Sigma) at 4° C. for one hour with gentle rocking. The glu-ag was spun down, and the supernatant discarded. Several washes with PBS were performed to remove residual bacterial proteins not adherent to the glu-ag. A final wash was performed in 50 mM Tris-Hcl pH 7.5. Fusion protein was specifically eluted from the agarose by the addition of 2 volumes (10 ml) of 50 mM Tris-HClpH 7.5, 5 mM glutathione. Yields of fusion protein are typically in the range of 15 mg/liter of bacterial culture.

EXAMPLE 5

Peptidyl-Prolyl Isomerase Activity

Cis-trans isomerization of peptide was measured in a coupled assay with chymotrypsin, which hydrolyses the anilide bond in the trans (but not cis) isomer (Fischer, 1989). Peptide cleavage was followed by monitoring the change in absorbance at 405 nm using a Bechman Du-65 spectrophotometer with a kinetics software module. A stock mixture containing peptide (final concentration 70 μm) in 100 mM Tris-HCl (pH 7.8) was mixed with GST or cyp C fusion protein plus or minus CsA. Nine hundred μl of each mixture was combined with 100 ul of chymotrypsin solution [0.66 mg/ml in Tris-HCl (pH 7.8)] to initiate the reaction. Data presented are the mean of three determinations. All procedures were carried out at 20° C.

EXAMPLE 6

Cell Culture and Preparation of Biosynthetically Labeled Protein

T cell lines and AC 6 were maintained in RPMI 1640 (Irvine Scientific) with 5% fetal bovine serum (Sigma), 1 mM sodium pyruvate (Irvine Scientific), 2 mM L-glutamine (Irvine Scientific) and $10^{-5}$M β-mercaptoethanol. Cells were cultured in humidified incubators at 37° C. with 7% $CO_2$. Confluent 10 cm dishes of AC 6, or the cells concentrated, from 10 ml of T cell cultures, were used for the preparation of radiolabeled proteins. Cultures were washed 1× with sterile PBS, and then placed for 30 minutes in MEM deficient in methionine and cysteine (Gibco), supplemented with 5% dialyzed fetal bovine serum. After 30 minutes, the medium was removed and replaced with 4 ml of deficient MEM plus 5% dialyzed serum. 250–500 $\mu Ci^{35}S$ methionine and 250–500 $\mu Ci^{35}S$ cysteine were added, and the cells were returned to the incubator. Labeling of AC 6 was carried out for a minimum of 6 hours and a maximum of 14 hours. T cell lines were grown in the presence of label for 2–4 hours. At the termination of the labeling incubation, cells were washed 2× with chilled PBS prior to harvesting.

Cell lysates were prepared by adding 2 ml of ice cold lysis buffer (150 mM NaCl, 50 mM Tris-HCl pH 7.5, 1 mM $MgCl_2$, 2 mM $CaCl_2$, 0.5% Triton X-100, 1 mM PMSF) directly to the washed AC 6 cells adherent to the plate, or to pelleted T cells on ice. AC 6 cell lysate was collected by scraping the dish with a rubber policeman. Lysates were spun 10 minutes in a microfuge at 4° C. to pellet nuclei and debris.

EXAMPLE 6

Cyp C Affinity Reactions $10^7$ TCA precipitable counts of labeled lysate were used per reaction. Reaction volumes were brought up to 1 ml in lysis buffer. Each reaction was precleared by incubation with 10 μg of glutathione-s-transferase (GST) and 100 μl of 50% glu-ag solution for 2 hours at 4° C. with gentle agitation. Reactions were spun 5 minutes in a microfuge at 4° C., and the pellets were discarded. To the precleared lysates, 10 μg of cyp C fusion protein was added, along with 30 μl of a 50% solution of glu-ag. Reactions were incubated at 4° with gentle agitation for 3–4 hours, at which time tubes were spun 5 minutes in a microfuge at 4° C., and the supernatants were removed. Glu-ag pellets were washed 4× with 1 ml of cold lysis buffer, being transferred to a fresh tube for the final wash. The was discarded, and the pellet was resuspended in 50–100 μl of SDS-PAGE sample buffer containing β-mercaptoethanol. Samples were boiled 5 minutes and loaded onto 9.5% SDS-PAGE gels. Gels were stained/fixed in methanol: acetic acid: coomassie blue, and destained in methanol: acetic acid. Gels were prepared for autoradiography by incubation in Enhance solution (NEN) followed by thorough rinsing and drying on cellophane membranes (Hoefer Scientific Instruments). Exposure duration for the gels shown was 7–10 days using Kodak XAR film.

EXAMPLE 7

Characterization of Cyclophilin C Clone

By use of the subtraction technique described in Example 1 (Rubenstein, 1990), we isolated several cDNA clones that are quantitatively or qualitatively up-regulated at the mRNA level when AC 6 cells are treated with the hematopoietic and inflammatory cytokine IL-1. One of the clones was a 1288 bp cDNA encoding a 212 amino acid protein, cyp C (FIGS. 1—1 and 1-2). Cyp C has a predicted molecular weight of 22,795 daltons, and a predicted pI of 7.37. Genomic DNA blots probed with labeled cyp C cDNA suggest that cyp C is a single copy gene distinct from cyclophilins A and B.

Hybridization with human genomic DNA under stringent conditions suggests that there is a closely related human homologue of cyp C. Using a panel of murine/hamster and murine/rat hybrid cell lines, the murine cyp C gene was mapped to chromosome 18.

FIGS. 2-1 and 2—2 show the extensive region of homology between cyp C and several previously-identified cyclophilins. Sequence alignments were generated using the Genalign program of Intelligenetics software. The region of homology extends from amino acid 36 to amino acid 205 of cyp C. The degree of homology within this overlap ranges from 77% identity (over 165 aa) with the human cyp B (Price, 1991), 58% identity (over 158 aa) with murine cyp A (Hasel, 1990), to 50% identity (over 165 aa) with the Drosophila ninaA gene (Schneuwly, 1989; Shieh, 1989). Within a core region of homology defined as stretching from aa 36 to aa 177 of cyp C, 46% of the residues are absolutely conserved among the five sequences compared. In comparing homologies over the entire sequences, it is evident that murine cyp A and yeast cyp 1 are more closely related to each other, while cyp C is more closely related to yeast cyp 2 and human cyp B than it is to either murine cyp A or yeast cyp 1. It is of interest to note that cyp C carries both amino and carboxyl terminal extensions relative to the previously isolated mammalian cyclophilin A proteins. In this regard, cyp C is similar to cyclophilins isolated from Drosophila, Neurospora (Tropschug, 1988), Saccharomyces (Koser, 1990), and recently, the human cyclophilin B (Price, 1991). The amino terminus contains a number of hydrophobic residues which might play a role in the intracellular localization of cyp C.

EXAMPLE 8

Tissue Specific Expression Profile of Cyclophilin C mRNA

Northern blot hybridizations (FIG. 3) reveal that cyp C is expressed in a restricted subset of tissues and cell lines. Increased expression of cyp C mRNA can be induced by IL-1 in the murine bone-marrow derived cell line AC 6 as can cyclophilin A. While liver expresses no detectable signal with cyp C, all tissues tested express cyclophilin A mRNA. Although cyclophilin A has been reported to be ubiquitous and highly abundant in its expression (Koletsky, 1986) we find that there are substantial variations in the amount of message present in the tissues assayed. Cyp C mRNA is expressed at relatively high levels in the kidney, as is cyclophilin A; this is of interest in light of evidence that CsA is highly nephrotoxic, but not generally hepatotoxic. It is possible that variations in the concentrations of cyclophilins A, B and C and perhaps other as yet unidentified members of the cyclophilin family determine the specific response of tissues to CsA.

EXAMPLE 9

Inhibition of Cyclophilin C by CsA

Figure 4:
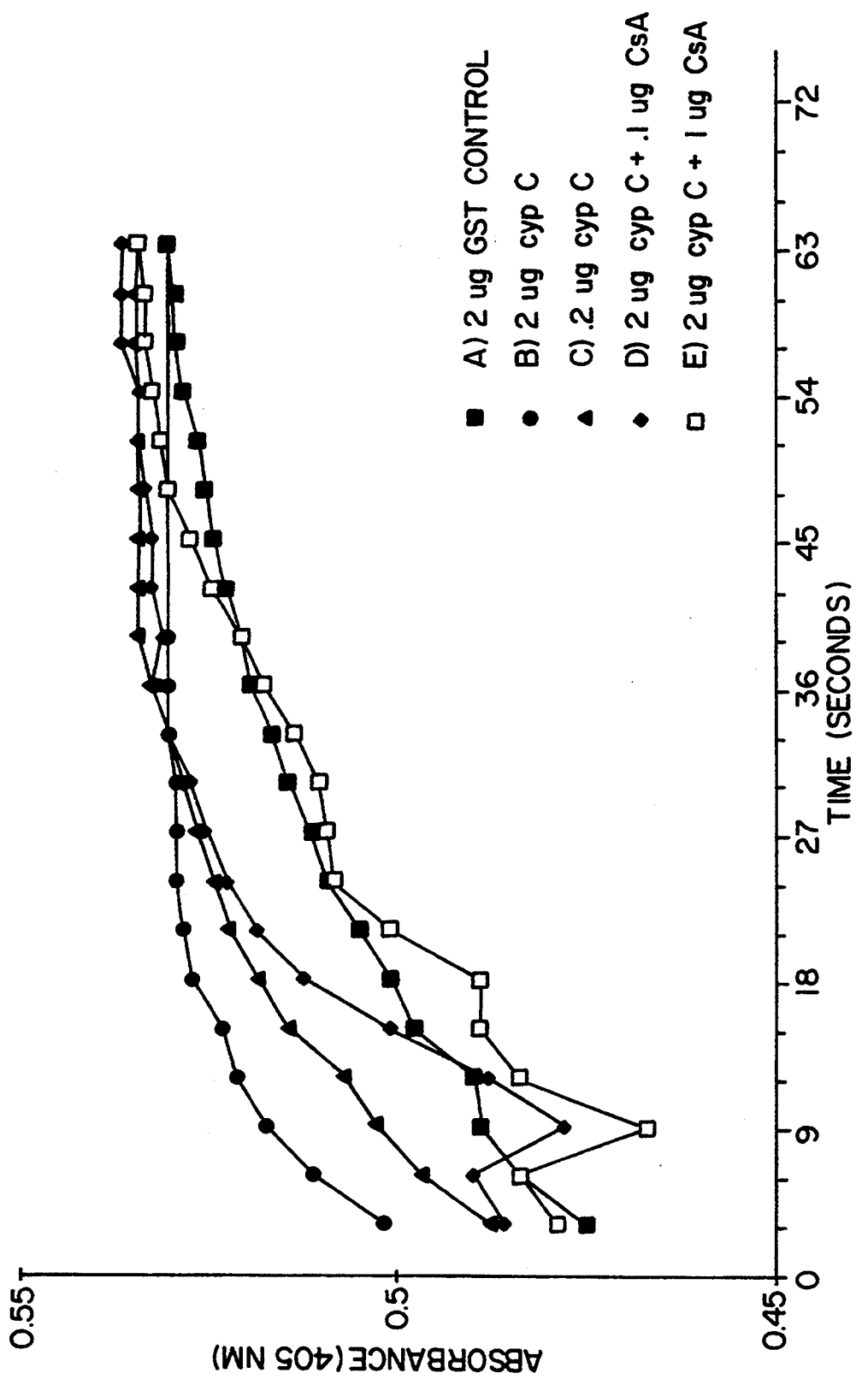
FIG. 4. Peptidyl-prolyl isomerase activity of cyp C and its inhibition by CsA. A stock mixture containing peptide (final concentration 70 $\mu$m) in 100 mM Tris-HCl (pH 7.8) was mixed with (A) 2 $\mu$g/ml glutathione-s-transferase (GST); (B) 2 $\mu$g/ml cyp C-GST fusion protein; (C) 0.2 $\mu$g/ml cyp C-GST fusion protein; (D) 2 $\mu$g/ml cyp C-GST fusion protein+0.1 $\mu$g/ml CsA; and (E) 2 $\mu$g/ml cyp C-GST fusion protein+1 $\mu$g/ml CsA. Reactions were initiated by the addition of a chymotrypsin solution.

A portion of the cyp C cDNA encoding aa 16–212 was cloned into the bacterial expression vector pGEX 2T (Smith, 1988) and a glutathione-s-transferase cyp C fusion protein was produced and purified. This fusion protein was assayed for cis-trans prolyl-isomerase activity. FIG. 4 shows the activity of the cyp C fusion protein, and the effect of CsA on this activity. Cis-trans isomerization of n-succinyl-Ala-Ala-Pro-Phe-paranitroanilide peptide was measured in a coupled assay with chymotrypsin, which hydrolyses the anilide bond in the trans (but not cis) isomer (Fischer, 1989). Addition of cyp C to the reaction accelerates the rate of cleavage of the peptide substrate in a concentration dependent manner (A versus B and C). The addition of CsA reverses the acceleration, also in a concentration dependent manner (B versus D and E). The drug FK506 had no effect on the PPIase activity of the cyp C fusion. These results demonstrate that cyp C possesses PPIase activity, and that this activity is blocked specifically by CsA.

EXAMPLE 10

Interaction of Cyclophilin C with Two Independent Cytoplasmic Proteins

The physiologic role of cyp C, as well as its role in the inhibition or facilitation of signal transduction, was explored by investigating its interactions with cytoplasmic proteins in the presence or absence of CsA. The GST-cyp C fusion protein was employed as an affinity ligand to search for cellular proteins with which it interacts. A glutathione agarose column was used to bind GST-cyp C protein, to which was added $^{35}$S methionine/$^{35}$S cysteine biosynthesized AC 6 cell lysate. After washing, the unlabelled GST-cyp C protein and its associated labelled AC 6 proteins were recovered by boiling in the presence of $\beta$-mercaptoethanol and SDS sample buffer.

Figure 5:
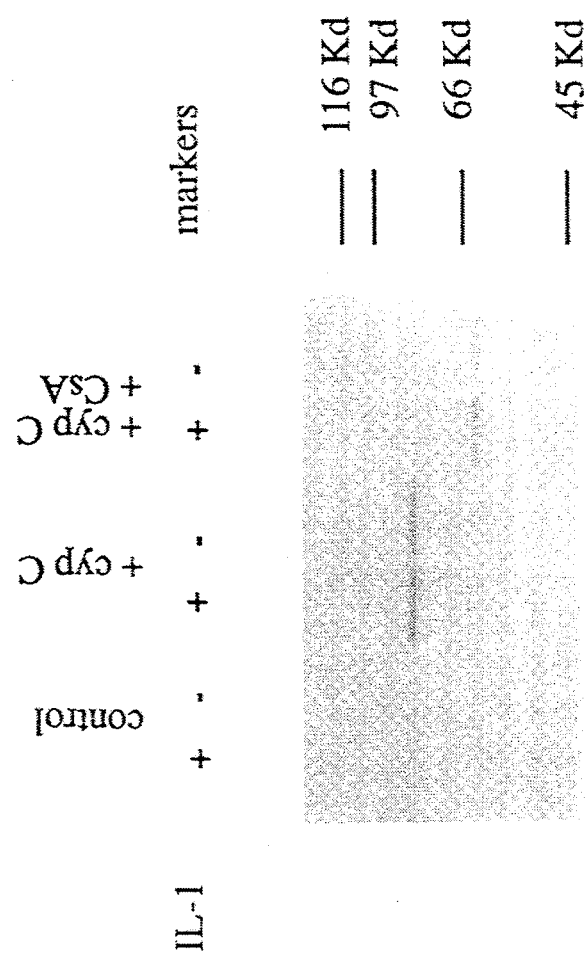
FIG. 5. Autoradiograph of SDS-PAGE gel of $^{35}$S methionine/cysteine labeled AC 6 proteins adherent to glutathione agarose plus 10 $\mu$g GST (control lanes); 10 $\mu$g cyp C-GST fusion protein (cyp C lanes); or 10 $\mu$g cyp C-GST fusion protein plus 10 $\mu$g/ml CsA (cyp C+CsA lanes). Cyp C affinity reactions were run as described below. The '+' denotes that the labeling was carried out in the presence of the cytokine IL-1; the '—' denotes that the labeling was carried out in the absence of IL-1.

FIG. 5 shows the results of such an affinity isolation. In this experiment the $^{35}$S methionine/cysteine labelled cell lysate from AC 6 was incubated with GST alone (control), cyp C fusion protein, or cyp C fusion plus CsA. A protein with an apparent molecular weight of ~77Kd binds to the cyp C fusion protein in the absence of CsA, while in the presence of CsA a protein with an apparent molecular weight of ~55Kd is bound. In the absence of CsA the p55 protein is not bound, while in the presence of CsA the p77 is not bound. The presence or absence of IL-1 in the culture media during the metabolic labeling has no obvious effect on these associating proteins.

Figure 6:
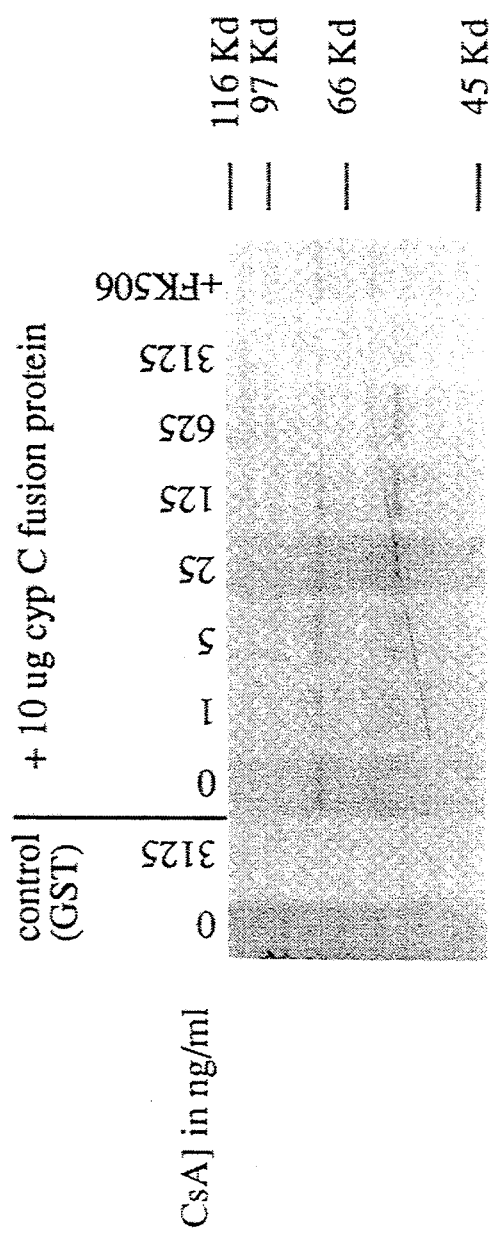
FIG. 6. Autoradiograph of SDS-PAGE gel of $^{35}$S methionine/cysteine labeled AC 6 proteins adherent to glutathione agarose plus fusion protein in the presence of increasing concentrations of CsA. Control samples were incubated with 10 $\mu$g of GST. Experimental samples were incubated with 10 μg of cyp C-GST fusion protein plus the indicated drug concentration.

The dependence on CsA concentration for the formation of cyp C:p77 vs cyp C:CsA:p55 complexes is explored in more detail in FIG. 6, in which increasing amounts of CsA were titrated into the reactions using a constant amount of fusion protein and labelled cellular proteins. In this experiment, when the concentration of CsA was increased to 5 ng/ml, the 55Kd band was clearly present as part of the complex. Above a CsA concentration of 125 ng/ml the intensity of the 55Kd band does not increase, suggesting that all available 55Kd protein is already complexed with the CsA:cyp C ligand. However, at concentrations of CsA greater than 125 ng/ml the intensity of the 77Kd band is incrementally reduced in intensity. A CsA concentration of ~2 $\mu$g/ml is sufficient to inhibit the isomerase activity of cyp C completely (FIG. 4), and by analogy with cyclophilin A it is likely that cyp C is nearly saturated with CsA under such conditions. Thus, very little free cyp C should be present at the highest CsA concentrations. These results suggest that the native cyp C protein is a high affinity ligand for the 77Kd protein, while the cyp C:CsA complex is a high affinity ligand for the 55Kd protein. The appearance of both bands in some lanes of FIG. 6 probably reflects both free and CsA bound forms of the cyp C fusion protein in those reactions. Addition of the immunosuppressive drug FK506 has no effect on the binding of cyp C to the 77Kd protein.

EXAMPLE 11

Figure 7:
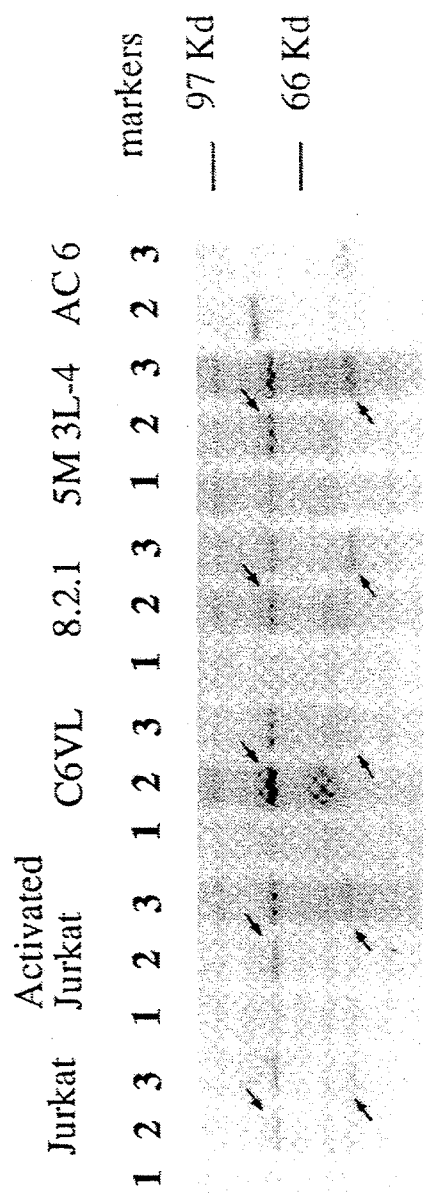
FIG. 7. Associating proteins in human and murine T cell lines. Cyp C affinity reactions were carried out using $^{35}$S labeled proteins from the human Jurkat line and the murine T cell lines C6VL, 8.2.1, and 5M3L-4. AC 6 proteins are run for size comparison of the 77Kd and 55Kd proteins. Lanes 1: (control) 10 μg of GST; Lanes 2: 10 μg cyp C-GST; Lanes 3: 10 μg cyp C-GST plus 5 μg/ml CsA. Activated Jurkat cells were prepared by incubation in the presence of phorbol myristate acetate (PMA) (20 ng/ml) and Ionomycin (2 μM) during the metabolic labeling.

Existence of Cyclophilin C Associating Proteins in Murine and Human T Cell Lines FIG. 7 shows the results of cyp C fusion protein reactions run with $^{35}$S methionine/cysteine labeled proteins prepared from the human jurkat T cell line and three murine T cell lines. All cell lines tested appear to have a 77Kd protein which binds in the absence of CsA (lanes 2). The murine cell lines and the human jurkat line also appear to have 55Kd proteins binding in the presence of CsA (lanes 3). In contrast to the AC 6 stromal cell lines, the T cell lines may contain other proteins that associate with these complexes, most prominently a band of ~70Kd. However, their presence does not require cyp C, and their intensities do not vary in a reproducible fashion with the presence or absence of CsA. The appearance of similar or identical proteins in murine and human T cell lines indicates the cross-species affinity of cyp C for its partner proteins, and may also indicate the utility of this protein in studying the mechanisms of action of CsA.

SELECTED REFERENCES

Bierer, B., Somers, P., Wandless, T., Burakoff, S., Schreiber, S. (1990). Probing Immunosuppressant Action with a Nonnatural Immunophilin Ligand. Science 250, 556–559.

Chmczynski, P., Sacchi, N. (1987). Single-step method of RNA isolation by acid guanidinium thiocyanate-phenol-chloroform extraction. Anal. Biochem, 162, 156–159.

Danielson, P., Forss-Petter, S., Brow, M., Calavetta, L., Douglass, J., Milner, R., Sutcliffe, J. (1988). p1B15: A cDNA clone of the Rat mRNA encoding cyclophilin. DNA 7, 261–267.

Dumont, F., Melino, M., Staruch, M., Koprak, S., Fischer, P., Sigal, N. (1990). The immunosuppressive macrolides FK-506 and Rapamycin act as reciprocal antagonists in murine T cells. J. Immunol. 144, 1418–1424.

Durette, P., Boger, J., Dumont, F., Firesone, R., Frankshun, R., Koprak, S., Lin, C., Melino, M., Pessolano, A., Pisano, J., Schmidt, J., Sigal, N., Staruch, M., Witzel, B. (1988). A study of the correlation between cyclophilin binding and in vitro immunosuppressive activity of cyclosporine A and analogues. Transplant Proc. 20, 51–57.

Emmel, E., Verweij, C., Durand, D., Higgins, K., Lacy, E., Crabtree, G. (1989). Cyclosporin A specifically inhibits function of nuclear proteins involved in T cell activation. Science 246, 1617–1620.

Fischer, G., Wittmann-Liebold, B., Lang, K., Kiefhaber, T., Schmid, F. (1989). Cyclophilin and peptidyl-prolyl cis-trans isomerase are probably identical proteins. Nature 337, 476–478.

Haendler, B., Hofer-Warbinek, R., Hofer, E. (1987). Complimentary DNA for human T-cell cyclophilin. EMBO J 6, 947–950.

Haendler, B., Keller, R., Hiestand P., Kocher, H., Wegmann, G., Rao Movva, N. (1989). Yeast cyclophilin: isolation and characterization of the protein, cDNA and gene. Gene 83, 39–46.

Handschumacher, R., Harding, M., Rice, J., Drugge, R. (1984). Cyclophilin: a specific cytosolic binding protein for cyclosporin A. Science 226, 544–547.

Harding, M., Galat, A., Uehling, D., Schreiber, S. (1989). A receptor for the immunosuppressant FK506 is a cis-trans peptidyl-prolyl isomerase. Nature 341, 758–760.

Hasel, K., Sutcliffe, J. (1990). Nucleotide sequence of a cDNA coding for mouse cyclophilin. Nuc. Acids Res. 18, 4019.

Hultsch, T., Rodriguez, J., Kaliner, M., Hohman, R. (1990). Cyclosporin A inhibits degranulation of rat Basophilic Leukemia cells and human Basophils. J. Immunol. 144, 2659–2664.

Koletsky, A., Harding, M., Handschumacher, R. (1986). Cyclophilin: distribution and variant properties in normal and neoplastic tissues. J. Immunol. 137, 1054–1059.

Koser, P., Syslvester, D., Livi, G., Bergsma, D. (1990). A second cyclophilin-related gene in Saccharomyces cerevisiae. Nuc. Acids Res. 18, 1643.

Laemmli, U. (1970). Cleavage of structural proteins during the assembly of the head of bacteriophage T4. Nature 227, 680–685.

Lovhaug, D., Pelus, L., Nordlie, E., Boyum, A., Moore, M. (1986). Monocyte-conditioned medium and interleukin 1 induce granulocyte-macrophage colony-stimulating factor production in the adherent cell layer of murine bone marrow cultures. Exp. Hematol 14, 1037–42.

Price, E., Zydowsky, L., Jin, M., Baker, C., McKeon, F., Walsh, C. (1991). Human cyclophilin B: A second cyclophilin gene encodes a peptidyl-prolyl isomerase with a signal sequence. Proc. Natl. Acad. Sci. U.S.A. 88, 1903–1907.

Porteus, M. H., Brice, E. J., Bulfone, A., Usdin, T. B., Ciaranello, R. D., Rubenstein, J. L. R. (1991). Isolation and characterization of a library of cDNA clones that are preferentially expressed in the embryonic telencephalon. Molecular Brain Research (in press).

Rubenstein, J., Brice, E., Ciaranello, R., Denney, D., Porteus, M., Usdin, T. (1990). Subtractive hybridization system using single-stranded phagemids with directional inserts. Nuc. Acids Res. 18, 4833–4842.

Saiki, R., Scharf, S., Faloona, F., Mullis, K. Horn, G., Erlich, H., Arnheim, N. (1985). Enzymatic amplification of beta-goblin genomic sequences and restriction site analysis for diagnosis of sickle cell anemia. Science 230, 1350–1354.

Sambrook, J., Fritsch, E.F., Maniatis, T., eds. (1989). Molecular Cloning. Cold Spring Harbor Laboratory Press.

Sanger, F., Nicklen, S., Coulson, A. (1977). DNA sequencing with chain-terminating inhibitors. Proc. Natl. Acad. Sci. 74, 5643.

Schneuwly, S. Shortridge, R., Larrivee, D., Ono, T., Ozaki, M., Pak, W. (1989). Drosophila nina A gene encodes an eye-specific cyclophilin (cyclosporine A binding Protein). Proc. Natl. Acad. Sci. 86, 5390–5394.

Schreiber, S. (1991). Chemistry and biology of the immunophilins and their immunosuppressive ligands. Science 251, 283–287.

Shieh, B., Stamnes, M., Seavello, S., Harris, G., Zuker, C. (1989). The ninaA gene required for visual transduction in Drosophila encodes a homologue of cyclosporin A-binding protein. Nature 338, 67–70.

Siekierka, J., Hung, S., Poe, M., Lin, C., Sigal, N. (1989). A cytosolic binding protein for the immunosuppressant FK506 has peptidyl-prolyl isomerase activity but is distinct from cyclophilin. Nature 341, 755–757.

Sigal, N., Dumont, F., Durette, P., Siekierka, J., Peterson, L., Rich, D., Dunlap, B., Staruch, M., Melino, M., Koprak, S., Williams, D., Witzel, B., Pisano, J. (1991). Is cyclophilin involved in the immunosuppressive and nephrotoxic mechanism of action of cyclosporin A? J. Exp. Med. 173, 619.

Smith, D., Johnson, K. (1988). Single-step purification of polypeptides expressed in Escherichia coli as fusions with glutathione S-transferase. Gene 67,40.

Stamnes, M., Shieh, G., Chuman, L., Harris, G., Zuker, C. (1991). The Cyclophilin Homolog ninaA Is a Tissue-Specific Integral Membrane Protein Required for the Proper Synthesis of a Subset of Drosophila Rhodopsins. Cell 65, 219–227.

Takahashi, N., Hayano, T., Suzuki, M. (1989). Peptidyl-prolyl cis-trans isomerase is the cyclosporin A-binding protein cyclophilin. Nature 337, 473–475.

Tocci, M., Matkovich, D., Collier, K., Kwok, P., Dumont, F., Lin, S., Degudicibus, S., Siekierka, J., Chin, J., Hutchinson, N. (1989). The immunosuppressant FK506 selectively inhibits expression of early T cell activation genes. J. Immunol. 143, 718–726.

Tropschug, M., Nicholson, D., Hartl, F., Kohler, H., Pfanner, N., Wachter, E., Neupert, W. (1988). Cyclosporin A-binding protein (cyclophilin) of Neurospora crassa. J. Biol. Chem. 263, 14433–14440.

Tropschug, M., Barthelmess, I., Neupert, W. (1989). Sensitivity to cyclosporin A is mediated by cyclophilin in Neurospora crassa and Saccharomyces cerevisiae. Nature 342, 953–955.

Whitlock, C., Tidmarsh, G.F., Muller-Sieburg, C., and Weissman, I.L. (1987). Bone marrow stromal cell lines with lymphopoietic activity express high levels of a pre-B neoplasia-associated molecule. Cell 48, 1009–21.

All publications, patents, and patent applications herein are incorporated by reference. The invention now being fully described, it will be apparent to one of ordinary skill in the art that many changes and modifications can be made thereto without departing from the spirit or scope of the appended claims.

We claim:

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: Primer ( i x ) FEATURE:
        ( A ) NAME/KEY: misc_feature
        ( B ) LOCATION: 1..41
        ( D ) OTHER INFORMATION: /note="Adaptor-Primer"

( x i ) SEQUENCE DESCRIPTION: SEQ ID NO:1:

```
GCATGCGCGC GGCCGCGGAG GCCTTTTTTT TTTTTTTTT T                          41
```

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

```
CTGGGATCCG TTGGTGTC                                                   18
```

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

```
GTCGACGGTA TCGATAAG                                                   18
```

( 2 ) INFORMATION FOR SEQ ID NO:4:

( i ) SEQUENCE CHARACTERISTICS:
        ( A ) LENGTH: 1288 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 53..691

( x i ) SEQUENCE DESCRIPTION: SEQ ID NO:4:

```
CCCGGAGCCT AAGGTTGCGC CCGTGCCATC GTTGCCACTT CCACCGCGCA CC ATG              55
                                                            Met
                                                            1

AGC CCG GGT CCC CGT CTG CTG CTG CCC GCG GTG CTC TGC CTG GGG CTT           103
Ser Pro Gly Pro Arg Leu Leu Leu Pro Ala Val Leu Cys Leu Gly Leu
          5               10                  15

GGA GCC CTG GTG TCT TCT TCG GGG TCC TCA GGC GTC CGA AAA CGA GGT           151
Gly Ala Leu Val Ser Ser Ser Gly Ser Ser Gly Val Arg Lys Arg Gly
         20              25              30

CCC TCG GTG ACG GAC AAG GTC TTC TTT GAT GTG AGG ATC GGA GAC AAA           199
Pro Ser Val Thr Asp Lys Val Phe Phe Asp Val Arg Ile Gly Asp Lys
     35              40              45

GAT GTG GGT AGA ATT GTG ATT GGC CTC TTT GGA AAC GTT GTA CCC AAG           247
Asp Val Gly Arg Ile Val Ile Gly Leu Phe Gly Asn Val Val Pro Lys
50              55              60              65

ACG GTG GAA AAC TTC GTG GCT CTG GCA ACA GGA GAG AAA GGC TAC GGG           295
Thr Val Glu Asn Phe Val Ala Leu Ala Thr Gly Glu Lys Gly Tyr Gly
             70              75              80

TAC AAG GGC AGC ATC TTC CAC CGT GTC ATC AAG GAC TTC ATG ATT CAA           343
Tyr Lys Gly Ser Ile Phe His Arg Val Ile Lys Asp Phe Met Ile Gln
         85              90              95

GGA GGG GAC TTC ACA GCT AGA GAT GGC ACT GGA GGG ATG AGC ATC TAT           391
Gly Gly Asp Phe Thr Ala Arg Asp Gly Thr Gly Gly Met Ser Ile Tyr
     100             105             110

GGT GAG ACA TTT CCG GAT GAG AAC TTC AAA CTG AAG CAC TAT GGC ATT           439
Gly Glu Thr Phe Pro Asp Glu Asn Phe Lys Leu Lys His Tyr Gly Ile
115             120             125

GGC TGG GTC AGC ATG GCC AAT GCT GGA CCA GAC ACC AAC GGA TCC CAG           487
Gly Trp Val Ser Met Ala Asn Ala Gly Pro Asp Thr Asn Gly Ser Gln
130             135             140             145

TTC TTC ATC ACC TTG ACC AAG CCC ACC TGG TTG GAT GGC AAA CAC GTT           535
Phe Phe Ile Thr Leu Thr Lys Pro Thr Trp Leu Asp Gly Lys His Val
             150             155             160

GTA TTT GGA AAA GTC CTA GAT GGG ATG ACT GTG GTA CAT TCC ATT GAA           583
Val Phe Gly Lys Val Leu Asp Gly Met Thr Val Val His Ser Ile Glu
         165             170             175

CTT CAA GCA ACA GAT GGC CAT GAC CGC CCA CTC ACC GAC TGC ACC ATC           631
Leu Gln Ala Thr Asp Gly His Asp Arg Pro Leu Thr Asp Cys Thr Ile
     180             185             190

GTC AAC AGT GGC AAG ATA GAT GTG AAA ACA CCC TTT GTG GTT GAG GTC           679
Val Asn Ser Gly Lys Ile Asp Val Lys Thr Pro Phe Val Val Glu Val
195             200             205

CCT GAT TGG TGACAGAAAT GGCGGAAGAC AGGAAACACA CTGGCTGGCC                   728
Pro Asp Trp
210

CATGTGCACA TCTGTGATCC ACCAGCAGTC TTTTAGTTAC TTAAAAGTTG TAGTTAAAAA         788

AATTTCTCAT TTAATTTTCC AGTCTCGATT GCAATAACAA AATCAACCAC ACAGTCAGAT         848

GTCTCAACAA ACACCTGTCA TCCCAGTATT TGGGAAGTGC AGGCAGGAGG ATCAGGGGTT         908
```

```
CAAGGCCAGC CTGGGCTAAC AGTAAGTTTG AGGCTAGCCT TGTCTGTTAC ATAAGTAATA        968

ACAATAAAAA TCAATCAAAG TCCTGCTCAG GAATTTTAAA TTGAACGACA TATCCTTCTT       1028

TTCTAGTGGT GCTATTTTCA AATCAAAAAA CTTTGCATTG CTATTTGTT TTTACAAACA        1088

TGGTTGAGTT TCACACGGTT CCTTGTGATC TCCATTTGGG TGACCCGAGG GTTTGTTTGA       1148

GGAAGGTGAC TATAATGAAG GTTAGCATTT TCTGTTCAAA TAGTTCTTGT TCAGGCAAAG       1208

GGAAATTTGA GTAGTATCAT ATGCTGTATA TCATGAGCAT TCTGGGGCTT GGTGTTCTTT       1268

ATAGTAAATA CTTTTTAATC                                                    1288
```

( 2 ) INFORMATION FOR SEQ ID NO:5:

( i ) SEQUENCE CHARACTERISTICS:
        ( A ) LENGTH: 212 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Ser Pro Gly Pro Arg Leu Leu Pro Ala Val Leu Cys Leu Gly
 1               5                  10                  15

Leu Gly Ala Leu Val Ser Ser Ser Gly Ser Gly Val Arg Lys Arg
            20                  25                  30

Gly Pro Ser Val Thr Asp Lys Val Phe Phe Asp Val Arg Ile Gly Asp
        35                  40                      45

Lys Asp Val Gly Arg Ile Val Ile Gly Leu Phe Gly Asn Val Val Pro
    50                  55                      60

Lys Thr Val Glu Asn Phe Val Ala Leu Ala Thr Gly Glu Lys Gly Tyr
65                      70                      75              80

Gly Tyr Lys Gly Ser Ile Phe His Arg Val Ile Lys Asp Phe Met Ile
                85                  90                  95

Gln Gly Gly Asp Phe Thr Ala Arg Asp Gly Thr Gly Gly Met Ser Ile
            100                 105                 110

Tyr Gly Glu Thr Phe Pro Asp Glu Asn Phe Lys Leu Lys His Tyr Gly
        115                 120                 125

Ile Gly Trp Val Ser Met Ala Asn Ala Gly Pro Asp Thr Asn Gly Ser
    130                 135                 140

Gln Phe Phe Ile Thr Leu Thr Lys Pro Thr Trp Leu Asp Gly Lys His
145                 150                 155                 160

Val Val Phe Gly Lys Val Leu Asp Gly Met Thr Val Val His Ser Ile
                165                 170                 175

Glu Leu Gln Ala Thr Asp Gly His Asp Arg Pro Leu Thr Asp Cys Thr
            180                 185                 190

Ile Val Asn Ser Gly Lys Ile Asp Val Lys Thr Pro Phe Val Val Glu
        195                 200                 205

Val Pro Asp Trp
    210
```

( 2 ) INFORMATION FOR SEQ ID NO:6:

( i ) SEQUENCE CHARACTERISTICS:
        ( A ) LENGTH: 205 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Met  Lys  Phe  Ser  Gly  Leu  Trp  Cys  Trp  Leu  Leu  Leu  Phe  Leu  Ser  Val
 1              5                        10                            15

Asn  Val  Ile  Ala  Ser  Asp  Val  Gly  Glu  Leu  Ile  Asp  Gln  Asp  Asp  Glu
              20                        25                       30

Val  Ile  Thr  Gln  Lys  Val  Phe  Phe  Asp  Ile  Glu  His  Gly  Glu  Glu  Ala
              35                        40                       45

Val  Gly  Arg  Ile  Val  Ile  Gly  Leu  Tyr  Gly  Lys  Phe  Cys  Pro  Lys  Thr
         50                        55                       60

Ala  Lys  Asn  Phe  Tyr  Lys  Leu  Ser  Thr  Thr  Thr  Asn  Ser  Lys  Lys  Gly
 65                       70                        75                            80

Phe  Ile  Gly  Ser  Thr  Phe  His  Arg  Val  Ile  Pro  Asn  Phe  Met  Val  Gln
                   85                        90                       95

Gly  Gly  Asp  Phe  Thr  Asp  Gly  Thr  Gly  Val  Gly  Gly  Lys  Ser  Ile  Tyr
              100                       105                     110

Gly  Asp  Thr  Phe  Pro  Asp  Glu  Asn  Phe  Thr  Leu  Lys  His  Asp  Arg  Lys
              115                       120                     125

Gly  Arg  Leu  Ser  Met  Ala  Asn  Arg  Gly  Lys  Asp  Thr  Asn  Gly  Ser  Gln
         130                       135                     140

Phe  Phe  Ile  Thr  Thr  Thr  Glu  Glu  Ala  Ser  Trp  Leu  Asp  Gly  Lys  His
145                      150                       155                           160

Val  Val  Phe  Gly  Gln  Val  Val  Asp  Gly  Met  Asp  Val  Val  Asn  Tyr  Ile
                   165                       170                     175

Gln  His  Val  Ser  Arg  Asp  Ala  Asn  Asp  Lys  Pro  Leu  Glu  Ala  Val  Lys
              180                       185                     190

Ile  Ala  Lys  Cys  Gly  Glu  Trp  Thr  Pro  Glu  Leu  Ser  Ser
         195                       200                     205
```

( 2 ) INFORMATION FOR SEQ ID NO:7:

( i ) SEQUENCE CHARACTERISTICS:
        ( A ) LENGTH: 208 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Met  Lys  Val  Leu  Leu  Ala  Ala  Ala  Leu  Ile  Ala  Gly  Ser  Val  Phe  Phe
 1              5                        10                            15

Leu  Leu  Leu  Pro  Gly  Pro  Ser  Ala  Ala  Asp  Glu  Lys  Lys  Lys  Gly  Pro
              20                        25                       30

Lys  Val  Thr  Val  Lys  Val  Tyr  Phe  Asp  Leu  Arg  Ile  Gly  Asp  Glu  Asp
              35                        40                       45

Val  Gly  Arg  Val  Ile  Phe  Gly  Leu  Phe  Gly  Lys  Thr  Val  Pro  Lys  Thr
         50                        55                       60

Val  Asp  Asn  Phe  Val  Ala  Leu  Ala  Thr  Gly  Glu  Lys  Gly  Phe  Gly  Tyr
 65                       70                        75                            80

Lys  Asn  Ser  Lys  Phe  His  Arg  Val  Ile  Lys  Asp  Phe  Met  Ile  Gln  Gly
                   85                        90                       95

Gly  Asp  Phe  Thr  Arg  Gly  Asp  Gly  Thr  Gly  Gly  Lys  Ser  Ile  Tyr  Gly
              100                       105                     110

Glu  Arg  Phe  Pro  Asp  Glu  Asn  Phe  Lys  Leu  Lys  His  Tyr  Gly  Pro  Gly
              115                       120                     125

Trp  Val  Ser  Met  Ala  Asn  Ala  Gly  Lys  Asp  Thr  Asn  Gly  Ser  Gln  Phe
         130                       135                     140

Phe  Ile  Thr  Thr  Val  Lys  Thr  Ala  Trp  Leu  Asp  Gly  Lys  His  Val  Val
145                      150                       155                           160
```

```
            Phe  Gly  Lys  Val  Leu  Glu  Gly  Met  Glu  Val  Val  Arg  Lys  Val  Glu  Ser
                           165                 170                      175

Thr  Lys  Thr  Asp  Ser  Arg  Asp  Lys  Pro  Leu  Lys  Asp  Val  Ile  Ile  Ala
                           180                      185                 190

Asp  Cys  Gly  Lys  Ile  Glu  Val  Glu  Lys  Pro  Phe  Ala  Ile  Ala  Lys  Glu
                           195                      200                      205
```

( 2 ) INFORMATION FOR SEQ ID NO:8:

( i ) SEQUENCE CHARACTERISTICS:
        ( A ) LENGTH: 163 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
            Val  Asn  Pro  Thr  Val  Phe  Phe  Asp  Ile  Thr  Ala  Asp  Asp  Glu  Pro  Leu
            1                   5                   10                      15

Gly  Arg  Val  Ser  Phe  Glu  Leu  Phe  Ala  Asp  Lys  Val  Pro  Lys  Thr  Ala
                           20                  25                      30

Glu  Asn  Phe  Arg  Ala  Leu  Ser  Thr  Gly  Glu  Lys  Gly  Phe  Gly  Tyr  Lys
                           35                  40                      45

Gly  Ser  Ser  Phe  His  Arg  Ile  Ile  Pro  Gly  Phe  Met  Cys  Gln  Gly  Gly
                           50                  55                      60

Asp  Phe  Thr  Arg  His  Asn  Gly  Thr  Gly  Gly  Arg  Ser  Ile  Tyr  Gly  Glu
            65                       70                      75                      80

Lys  Phe  Glu  Asp  Glu  Asn  Phe  Ile  Leu  Lys  His  Thr  Gly  Pro  Gly  Ile
                           85                  90                      95

Leu  Ser  Met  Ala  Asn  Ala  Gly  Pro  Asn  Thr  Asn  Gly  Ser  Gln  Phe  Phe
                           100                 105                     110

Ile  Cys  Thr  Ala  Lys  Thr  Glu  Trp  Leu  Asp  Gly  Lys  His  Val  Val  Phe
                           115                 120                     125

Gly  Lys  Val  Lys  Glu  Gly  Met  Asn  Ile  Val  Glu  Ala  Met  Glu  Arg  Phe
                           130                 135                     140

Gly  Ser  Arg  Asn  Gly  Lys  Thr  Ser  Lys  Lys  Ile  Thr  Ile  Ser  Asp  Cys
            145                      150                     155                     160

Gly  Gln  Leu
```

( 2 ) INFORMATION FOR SEQ ID NO:9:

( i ) SEQUENCE CHARACTERISTICS:
        ( A ) LENGTH: 162 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
            Met  Ser  Gln  Val  Tyr  Phe  Asp  Val  Glu  Ala  Asp  Gly  Gln  Pro  Ile  Gly
            1                   5                   10                      15

Arg  Val  Val  Phe  Lys  Leu  Tyr  Asn  Asp  Ile  Val  Pro  Lys  Thr  Ala  Glu
                           20                  25                      30

Asn  Phe  Arg  Ala  Leu  Cys  Thr  Gly  Glu  Lys  Gly  Phe  Gly  Tyr  Ala  Gly
                           35                  40                      45

Ser  Pro  Phe  His  Arg  Val  Ile  Pro  Asp  Phe  Met  Leu  Gln  Gly  Gly  Asp
                           50                  55                      60

Phe  Thr  Ala  Gly  Asn  Gly  Thr  Gly  Gly  Lys  Ser  Ile  Tyr  Gly  Gly  Lys
            65                       70                      75                      80
```

|  |  |  |  |  |  |  |  |  |  |  |  |  |  |  |
|---|---|---|---|---|---|---|---|---|---|---|---|---|---|---|
| Phe | Pro | Asp | Glu | Asn<br>85 | Phe | Lys | Lys | His | His<br>90 | Asp | Arg | Pro | Gly | Leu Arg<br>95 |
| Ser | Met | Ala | Asn<br>100 | Ala | Gly | Pro | Asn | Thr<br>105 | Asn | Gly | Ser | Gln | Phe<br>110 | Phe Ile |
| Thr | Thr | Val<br>115 | Pro | Cys | Pro | Trp | Leu<br>120 | Asp | Gly | Lys | His | Val<br>125 | Val | Phe Gly |
| Glu | Val<br>130 | Val | Asp | Gly | Tyr | Asp<br>135 | Ile | Val | Lys | Lys | Val<br>140 | Glu | Ser | Leu Gly |
| Ser<br>145 | Pro | Ser | Gly | Ala | Thr<br>150 | Lys | Ala | Arg | Ile<br>155 | Val | Val | Ala | Lys | Ser Gly<br>160 |
| Glu | Leu |  |  |  |  |  |  |  |  |  |  |  |  |  |

( 2 ) INFORMATION FOR SEQ ID NO:10:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:10:

ATAAGCTTGA TGGGC                                                                                        15

1. An isolated polynucleotide encoding a mammalian cyclophilin c polypeptide, comprising a polynucleotide sequence encoding an amino acid sequence comprising about at least 197 contiguous amino acids of the deduced cyclophilin c amino acid sequence shown in SEQ. ID NO:5 and having prolyl isomerase activity.

2. An isolated polynucleotide of claim 1, wherein said mammalian cyclophilin c polypeptide has prolyl isomerase activity which is inhibited by the presence of cyclosporin A.

3. An isolated polynucleotide of claim 1, wherein the encoded mammalian cyclophilin c polypeptide comprises the 212 amino acid sequence shown in SEQ. ID NO:5.

4. An isolated polynucleotide of claim 3, wherein the polynucleotide comprises the nucleotide Sequence from nucleotide 53 to nucleotide 688 of the nucleotide sequence shown in SEQ. ID NO:4.

5. An isolated polynucleotide of claim 1, wherein the encoded mammalian cyclophilin c polypeptide is a fusion protein comprising at least 197 contiguous amino acids of the deduced cyclophilin c amino acid sequence shown in SEQ. ID NO:5 in polypeptide linkage to a heterologous or homologous polypeptide sequence, wherein the fusion protein has prolyl isomerase activity.

6. An isolated polynucleotide of claim 5, wherein the prolyl isomerase activity is inhibited by the presence of cyclosporin A.

7. An isolated polynucleotide of claim 5, wherein the fusion protein comprises a glutathione S-transferase polypeptide sequence.

8. An isolated polynucleotide encoding the 212 amino acid sequence shown in SEQ. ID NO:5.

9. An isolated polynucteotide encoding a polypeptide having a sequence of at least 197 contiguous amino acids wherein said sequence is identical to a cyclophilin c sequence spanning amino acid 16 to amino acid 212 of the amino acid sequence shown in SEQ. ID NO:5 or a sequence differing from said cyclophilin c sequence by only conservative amino acid substitution and wherein. said encoded polypeptide has prolyl isomerase activity.

10. An isolated polynucleotide according to claim 9, wherein said polynucleotide encodes a polypeptide of at least 212 contiguous amino acids wherein said sequence is identical to the amino acid sequence shown in SEQ. ID NO:5 or a sequence differing from said amino acid sequence by only conservative amino acid substitution and wherein said encoded polypeptide has prolyl isomerase activity.

11. An isolated polynucleotide of claim 1 or 9, wherein the polynucleotide is attached to a label or reporter molecule.

12. A recombinant DNA vector comprising a polynucleotide of claim 1 or 9.

13. A host cell transformed with a recombinant DNA vector of claim 12.

14. A host cell of claim 13 which expresses a cyclophilin c polypeptide under suitable culture conditions.

15. A method of producing a cyclophilin c polypeptide comprising culturing a host cell of claim 14 under suitable culture conditions whereby said host cell expresses said cyclophilin c polypeptide, and recovering said polypeptide.

16. A recombinant DNA vector, wherein the vector is an expression vector comprising a promoter operably linked to a polynucleotide of claim 1 or 9.

17. A recombinant DNA vector of claim 16, wherein the expression vector expresses a cyclophilin c polypeptide in a suitable prokaryotic host cell.

* * * * *